United States Patent
Yoo et al.

(10) Patent No.: US 12,201,258 B2
(45) Date of Patent: *Jan. 21, 2025

(54) SHOE MANAGEMENT APPARATUS

(71) Applicant: LG ELECTRONICS INC., Seoul (KR)

(72) Inventors: Hyunsun Yoo, Seoul (KR); Jeong Guen Choi, Seoul (KR); Joohyeon Oh, Seoul (KR); Jae Myung Lim, Seoul (KR); Byoungjoon Han, Seoul (KR); Sang Yoon Lee, Seoul (KR); Hyunju Kim, Seoul (KR); Jeaseok Seong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 753 days.

This patent is subject to a terminal disclaimer.

(21) Appl. No.: 17/356,298

(22) Filed: Jun. 23, 2021

(65) Prior Publication Data
US 2021/0401266 A1 Dec. 30, 2021

(30) Foreign Application Priority Data

| | | |
|---|---|---|
| Jun. 24, 2020 | (KR) | 10-2020-0077410 |
| Jun. 24, 2020 | (KR) | 10-2020-0077411 |
| Jun. 24, 2020 | (KR) | 10-2020-0077412 |
| Jun. 24, 2020 | (KR) | 10-2020-0077413 |
| Jun. 24, 2020 | (KR) | 10-2020-0077414 |

(Continued)

(51) Int. Cl.
*A47L 23/20* (2006.01)
*A61L 2/26* (2006.01)

(52) U.S. Cl.
CPC .............. *A47L 23/205* (2013.01); *A61L 2/26* (2013.01); *A61L 2202/122* (2013.01); *A61L 2202/15* (2013.01); *A61L 2202/26* (2013.01)

(58) Field of Classification Search
CPC .... A47L 23/205; A61L 2/26; A61L 2202/122; A61L 2202/15; A61L 2202/26
(Continued)

(56) References Cited

U.S. PATENT DOCUMENTS

| | | | | |
|---|---|---|---|---|
| 1,667,315 A | * | 4/1928 | Harris | A43D 11/14 8/94.2 |
| 2,089,783 A | * | 8/1937 | Chace | A43D 95/12 211/144 |

(Continued)

FOREIGN PATENT DOCUMENTS

| | | |
|---|---|---|
| CN | 102907914 A | 2/2013 |
| CN | 104687789 A | 6/2015 |

(Continued)

*Primary Examiner* — Stephen M Gravini
(74) *Attorney, Agent, or Firm* — Birch, Stewart, Kolasch & Birch, LLP

(57) ABSTRACT

A shoe management apparatus including a receiving portion defining a receiving space for receiving shoes therein, a first supply portion for guiding flow of a fluid towards the receiving portion, the first supply portion including a stationary duct disposed above the receiving space, a flexible duct connected to the stationary duct and able to rotate to change shape, a rotatable duct connected to the flexible duct and a first driver connected to the rotatable duct and for generating a rotational force to rotate the rotatable duct.

20 Claims, 23 Drawing Sheets

(30) Foreign Application Priority Data

| Jun. 24, 2020 | (KR) | 10-2020-0077415 |
| Jun. 24, 2020 | (KR) | 10-2020-0077417 |
| Dec. 8, 2020 | (KR) | 10-2020-0170566 |
| Mar. 9, 2021 | (KR) | 10-2021-0030923 |

(58) Field of Classification Search
  USPC .......................................................... 34/104
  See application file for complete search history.

(56) References Cited

U.S. PATENT DOCUMENTS

| | | | | |
|---|---|---|---|---|
| 3,203,112 | A * | 8/1965 | Edmonds | A47L 23/205 34/437 |
| 4,171,580 | A * | 10/1979 | Vabrinskas | A47L 23/20 34/239 |
| 5,179,790 | A | 1/1993 | Poulos | |
| 5,720,108 | A * | 2/1998 | Rice | D06F 59/04 34/104 |
| 6,094,767 | A | 8/2000 | Iimura | |
| 6,675,425 | B1 | 1/2004 | Iimura | |
| 6,796,053 | B2 * | 9/2004 | Lurie | F26B 21/006 34/239 |
| 6,845,569 | B1 * | 1/2005 | Kim | A47L 23/20 34/106 |
| 6,880,711 | B2 | 4/2005 | Collier | |
| 7,043,854 | B2 * | 5/2006 | Peet | A47L 23/205 34/104 |
| 7,121,017 | B2 * | 10/2006 | DuRapau | A47L 23/205 34/437 |
| 8,186,075 | B2 * | 5/2012 | Beckett | A47L 23/205 34/106 |
| 10,143,354 | B2 * | 12/2018 | Putnam, Jr. | F26B 9/003 |
| 11,408,679 | B2 * | 8/2022 | Ohnari | F26B 25/008 |
| 2006/0137210 | A1 | 6/2006 | Lee et al. | |
| 2011/0053641 | A1 | 3/2011 | Lee et al. | |
| 2015/0040211 | A1 | 2/2015 | Lee et al. | |
| 2017/0192530 | A1 | 7/2017 | Lee et al. | |
| 2018/0015196 | A1 | 1/2018 | Huang et al. | |
| 2018/0156535 | A1 | 6/2018 | Kim | |
| 2019/0323765 | A1 | 10/2019 | Kim | |
| 2020/0149802 | A1 | 5/2020 | Kim | |
| 2020/0173715 | A1 | 6/2020 | Kim | |
| 2021/0071345 | A1 | 3/2021 | Lee et al. | |
| 2021/0299311 | A1 | 9/2021 | Yu | |
| 2021/0401127 | A1 * | 12/2021 | Yoo | A43D 3/1408 |
| 2021/0401266 | A1 * | 12/2021 | Yoo | A61L 2/26 |
| 2023/0346194 | A1 * | 11/2023 | Lv | A47F 7/08 |

FOREIGN PATENT DOCUMENTS

| | | | |
|---|---|---|---|
| CN | 109106086 A | 1/2019 | |
| CN | 109674436 A | 4/2019 | |
| CN | 209171826 U | 7/2019 | |
| CN | 112438681 A | 3/2021 | |
| CN | 115768329 A * | 3/2023 | ............ A47B 61/04 |
| JP | 2-6543 U | 1/1990 | |
| JP | 5-192291 A | 8/1993 | |
| JP | 5-337002 A | 12/1993 | |
| JP | 3023965 U | 2/1996 | |
| JP | 9-253595 A | 9/1997 | |
| JP | 11-103941 A | 4/1999 | |
| JP | 2008-86419 A | 4/2008 | |
| JP | 2010-119609 A | 6/2010 | |
| JP | 10-2020-0002725 A | 1/2020 | |
| KR | 20-0165450 Y1 | 2/2000 | |
| KR | 20-0187262 Y1 | 7/2000 | |
| KR | 20-0253977 Y1 | 11/2001 | |
| KR | 20-0291502 Y1 | 10/2002 | |
| KR | 20-0307594 Y1 | 3/2003 | |
| KR | 10-0407908 B1 | 12/2003 | |
| KR | 20-0357295 Y1 | 7/2004 | |
| KR | 10-2004-0070545 A | 8/2004 | |
| KR | 20-0397164 Y1 | 9/2005 | |
| KR | 10-2006-0060230 A | 6/2006 | |
| KR | 10-0590794 B1 | 6/2006 | |
| KR | 20-0426182 Y1 | 9/2006 | |
| KR | .20-0431598 Y1 | 11/2006 | |
| KR | 10-2008-0006908 A | 1/2008 | |
| KR | 20-2011-0011197 U | 12/2011 | |
| KR | 10-2012-0059781 A | 6/2012 | |
| KR | 10-2012-0092800 A | 8/2012 | |
| KR | 10-2014-0106818 A | 9/2014 | |
| KR | 10-2015-0086056 A | 7/2015 | |
| KR | 10-2015-0117430 A | 10/2015 | |
| KR | 10-2015-0123493 A | 11/2015 | |
| KR | 10-2017-0024363 A | 3/2017 | |
| KR | 10-2017-0039412 A | 4/2017 | |
| KR | 10-1737829 B1 | 5/2017 | |
| KR | 10-2018-0054004 A | 5/2018 | |
| KR | 10-2019-0003274 A | 1/2019 | |
| KR | 10-1938421 B1 | 1/2019 | |
| KR | 10-2008104 B1 | 8/2019 | |
| KR | 10-2019-0128460 A | 11/2019 | |
| KR | 10-2020-0031889 A | 3/2020 | |
| KR | 10-2020-0037035 A | 4/2020 | |
| WO | WO-2021261742 A1 * | 12/2021 | ............ A47B 61/04 |

* cited by examiner

SHOE MANAGEMENT APPARATUS

CROSS-REFERENCE TO RELATED APPLICATIONS

This application claims priority to and the benefit of Korean Patent Application No. Korean Patent Application No. 10-2020-0077410 filed on Jun. 24, 2020, Korean Patent Application No. 10-2020-0077411 filed on Jun. 24, 2020, Korean Patent Application No. 10-2020-0077412 filed on Jun. 24, 2020, Korean Patent Application No. 10-2020-0077413 filed on Jun. 24, 2020, Korean Patent Application No. 10-2020-0077414 filed on Jun. 24, 2020, Korean Patent Application No. 10-2020-0077415 filed on Jun. 24, 2020, Korean Patent Application No. 10-2020-0077417 filed on Jun. 24, 2020, Korean Patent Application No. 10-2020-0170566 filed on Dec. 8, 2020, and Korean Patent Application No. 10-2021-0030923, filed on Mar. 9, 2021, the disclosures of which are incorporated herein by reference in their entirety into the present application.

BACKGROUND OF THE INVENTION

1. Field of the Invention

The present disclosure relates to a shoe management apparatus that facilitates drying of the interior of shoes.

2. Description of the Background Art

In general, shoes worn every day become sweaty due to use for a long period of time, thereby causing propagation of various germs therein, which generates foul odors and make it difficult to keep the shoes clean.

In rainy weather, since shoes are wet with rain, moisture and germs can be generated in the shoes, thereby causing problems of foul odors and reduced foot health due to the propagation of germs.

Washing or natural drying is performed to remove such moisture and germs from the interior of the shoes. However, since washing or natural drying of the shoes is cumbersome and takes a long time, it is difficult to wash or naturally dry the shoes and thus to wear clean shoes every day.

In order to address such problems, a prior technique (KR Patent Laid-open Publication No. 10-2020-0031889) provides a circular arrangement mounting type shoe dryer. The prior technique includes: an input port connected to a heater to supply hot air into an interior space; a drying room having a discharge port through which inner air is discharged; a rotatable duct rotatably provided to an inner bottom surface or an upper surface of the drying room and provided with multiple distribution holes through which the hot air supplied through the input port is divided and supplied; and mounting pipes connected at one end thereof to the distribution holes of the rotatable duct to protrude at an upward angle such that shoes can be inserted downwardly into the mounting pipes, and provided with multiple ejection holes to eject the hot air supplied through the distribution holes in all directions.

However, in the prior technique, since the mounting pipes are always exposed outside, there is a problem of interference between the shoes and the mounting pipes when the shoes are received or taken out of the dryer.

Moreover, since the mounting pipes are disposed in a hanger shape, there is a problem that shoes disposed at a lower side can be contaminated with foreign substances falling from other shoes disposed at an upper side. That is, foreign substances can be washed off from shoes at the upper side and fall toward the shoes at the lower side, thus contaminating the shoes at the lower side.

Moreover, the prior technique allows only low-height shoes, such as sneakers, to be dried and cannot dry high-height shoes, such as boots, which have a greater height than the sneakers. Therefore, there is a need for solve such problems of the prior technique.

The background technique of the present disclosure is disclosed in KR Patent Laid-open Publication No. 10-2020-0031889 (Publication Date: 2020 Mar. 25, Title of the Invention: Circular arrangement mounting type shoe dryer).

SUMMARY OF THE INVENTION

Embodiments of the present disclosure provide a shoe management apparatus that can prevent interference between shoes and other components upon placement of the shoes in the shoe management apparatus or upon removal of the shoes therefrom.

Embodiments of the present disclosure provide a shoe management apparatus that can prevent contamination of shoes by foreign substances falling from other shoes upon drying or sterilization of the shoes.

Embodiments of the present disclosure provide a shoe management apparatus that allows low-height shoes, such as sneakers, to be dried together with high-height shoes, such as boots, having a greater height than the sneakers.

Objectives of the present disclosure are not limited to what has been described.

Additionally, other objectives and advantages that have not been mentioned may be clearly understood from the following description and may be more clearly understood from embodiments. Further, it will be understood that the objectives and advantages of the present disclosure may be realized via means and a combination thereof that are described in the appended claims.

To solve the above problems, a shoe management apparatus according to the present disclosure prevents interference between shoes and other components upon placement of the shoes in the shoe management apparatus or upon removal of the shoes therefrom.

Specifically, since a first supply portion is disposed inside a receiving portion before or after drying of the shoes is performed, the shoes are prevented from interfering with other components upon placement of the shoes in the receiving portion or upon removal of the shoes therefrom, thereby enabling more convenient management of the shoes.

In addition, the shoe management apparatus according to the present disclosure allows low-height shoes, such as sneakers, to be dried together with high-height shoes, such as boots, having a greater height than the sneakers.

Specifically, since the first supply portion is rotated to a lower side in consideration of the heights of the shoes, the shoe management apparatus allows low-height shoes, such as sneakers, to be dried together with high-height shoes, such as boots, having a greater height than the sneakers.

According to one embodiment, the shoe management apparatus includes at least one of a casing, a receiving portion, a first supply portion, a second supply portion, a third supply portion, a rotation-restricting portion, a height measurement unit, and a controller.

According to one embodiment, the shoe management apparatus may include: a receiving portion defining a receiving space for receiving shoes therein; and a first supply portion disposed at an upper side of the receiving portion and supplying air towards the receiving portion through bending operation of a duct guiding flow of the air therein.

The first supply portion may include: a stationary duct disposed at an upper side of the receiving space and restricted in movement; a flexible duct connected to the stationary duct and having a shape changed by rotation thereof; a rotatable duct connected to the flexible duct and moved into the receiving space through rotation thereof; and a first driver connected to the rotatable duct and generating rotational force rotating the rotatable duct.

The first supply portion may include a stationary housing secured to the receiving portion and having an interior space in which the rotatable duct rotated to the upper side of the receiving portion is placed.

The first supply portion may include a blower disposed next to the stationary duct and supplying air into the stationary duct.

The flexible duct may define a duct channel having multiple bent shapes such that air can flow into the rotatable duct along a zigzag shape through the flexible duct.

The electric compartment may be provided with a steam generator supplying steam for sterilization to the first supply portion.

The first supply portion may further include a heat exchanger disposed next to the blower and performing heat exchange with air flowing into the blower.

In the shoe management apparatus according to the present disclosure, since the first supply portion is disposed inside the receiving portion before or after drying of shoes is performed, the shoes are prevented from interfering with other components upon placement of the shoes in the receiving portion or upon removal of the shoes from the receiving portion, thereby improving user convenience.

In addition, the shoe management apparatus according to the present disclosure allows low-height shoes, such as sneakers, to be dried together with high-height shoes, such as boots, having a greater height than the sneakers, thereby reducing installation costs of the shoe management apparatus.

Further, in the shoe management apparatus according to the present disclosure, the first supply portion is rotated towards the interior of the receiving portion to be disposed in a bent shape therein, thereby reducing time and costs for drying the shoes through increase in flow rate of a fluid supplied to the shoes.

Further, when the first supply portion is not operated, the first supply portion is stably stored inside the stationary housing, thereby improving durability of components of the shoe management apparatus.

Further, the blower is operated to increase the flow rate of air supplied into the stationary duct, thereby reducing time for drying the shoes.

Further, the shoe management apparatus allows air supplied into the rotatable duct through the flexible duct to flow in a zigzag shape, thereby enabling uniform drying of the shoes.

Further, in the shoe management apparatus according to the present disclosure, steam generated by the steam generator is supplied to the shoes, thereby reducing time for sterilization and deodorization of the shoes.

Further, in the shoe management apparatus according to the present disclosure, the heat exchanger is operated to regulate temperature of the fluid supplied to the shoes, thereby reducing time for drying the shoes.

The above and other effects of the present disclosure will become apparent from description of details of the present disclosure.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

Figure 1:
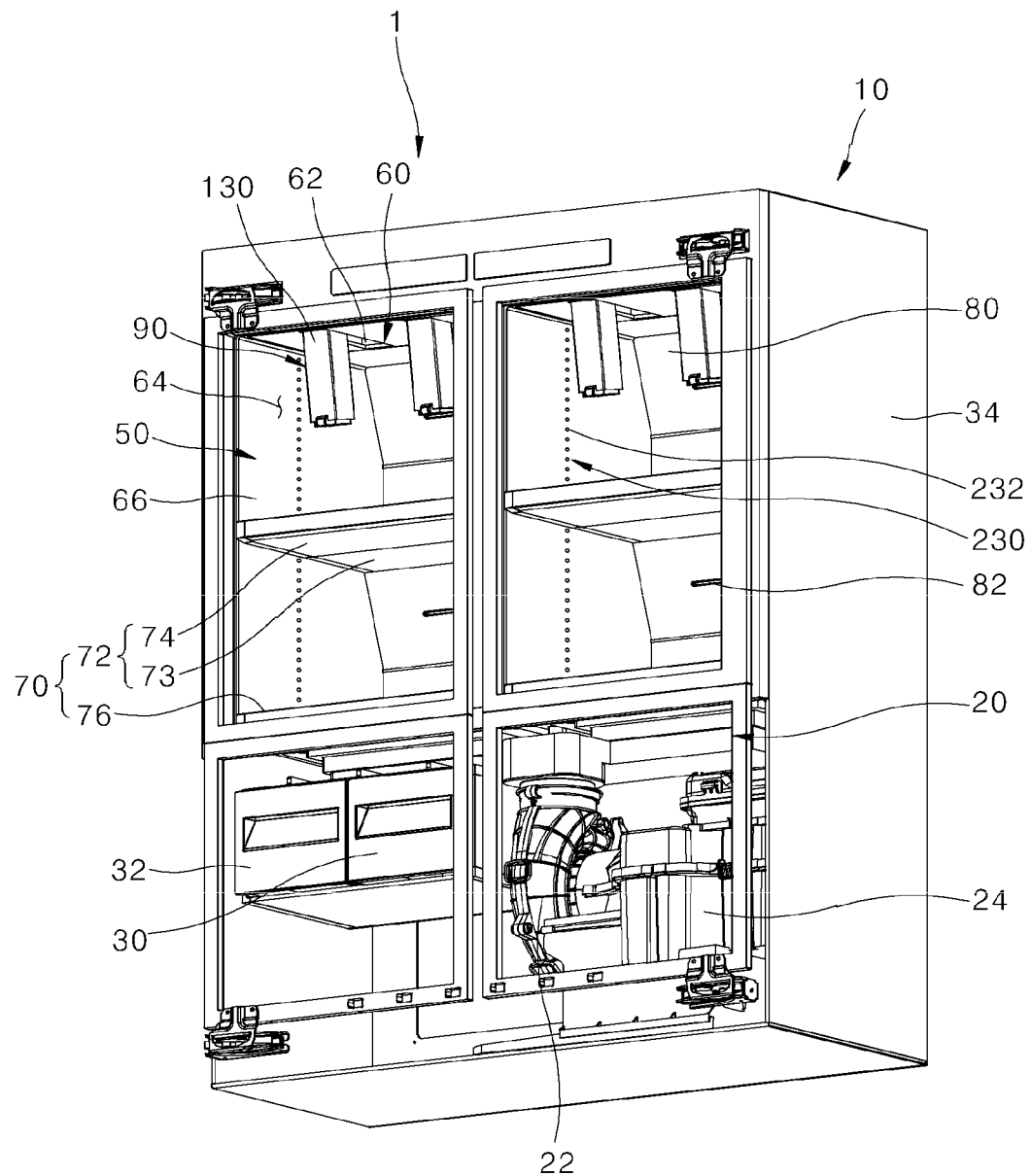
FIG. 1 is a front perspective view of a shoe management apparatus according to an embodiment of the present disclosure.

The above and other aspects, features, and advantages of the present disclosure will be described in more detail in conjunction with the accompanying drawings so as to fully convey the spirit of the present disclosure to those skilled in the art. Descriptions of known functions and constructions which can unnecessarily obscure the subject matter of the present disclosure will be omitted. Hereinafter, embodiments of the present disclosure will be described in detail with reference to the accompanying drawings. Like components will be denoted by like reference numerals throughout the accompanying drawings.

[Overall Configuration of Shoe Management Apparatus]

Figure 9:
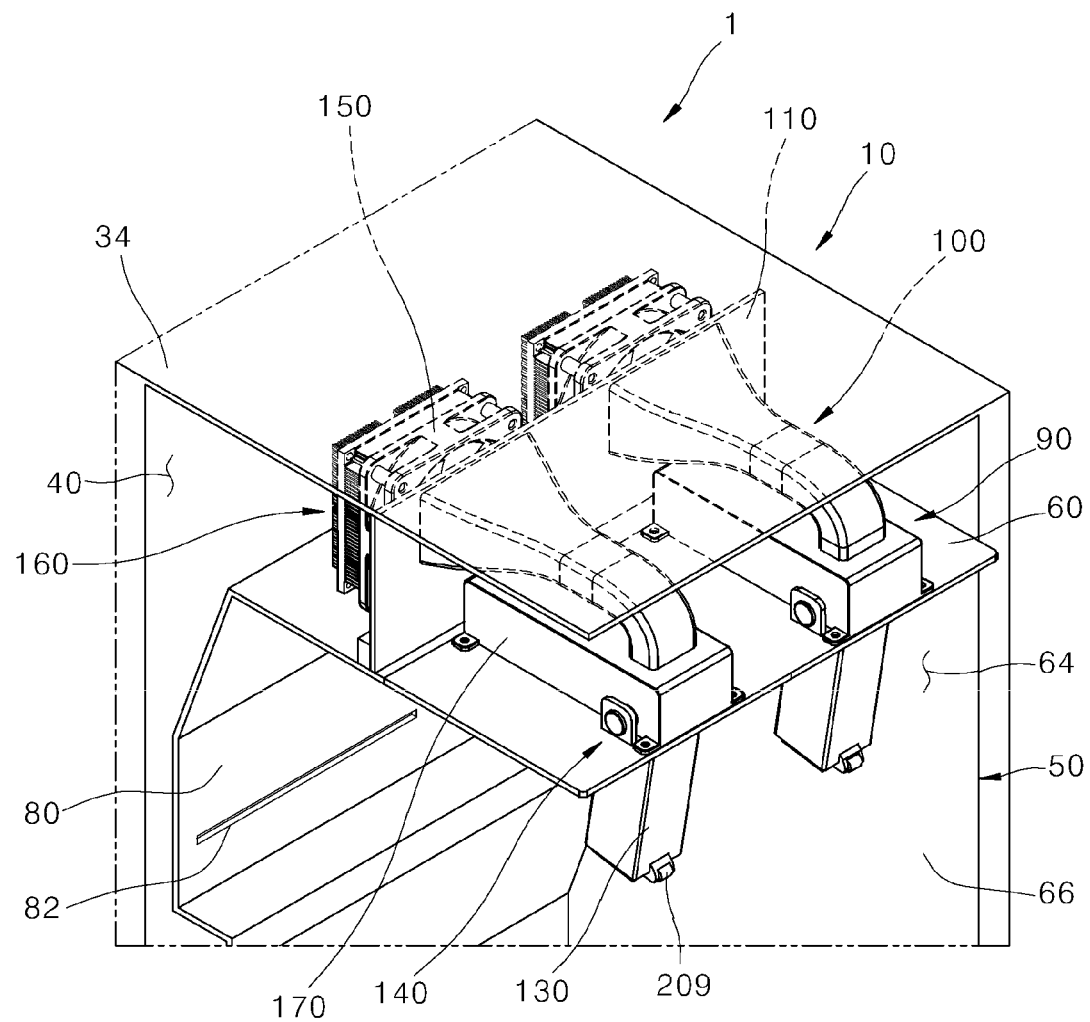
FIG. 9 is a perspective view of an interior flow channel of the shoe management apparatus according to the embodiment of the present disclosure.
Figure 10:
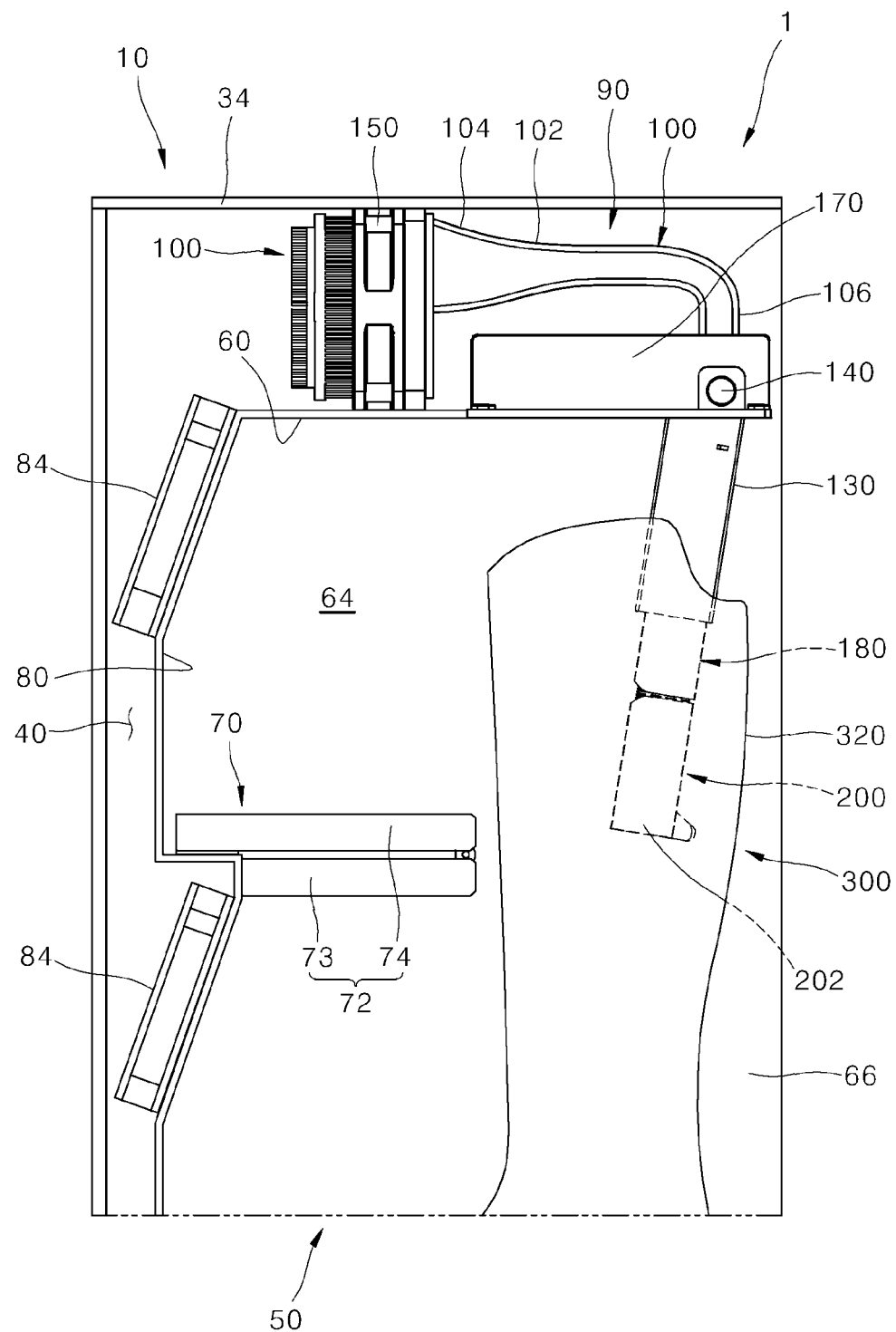
FIG. 10 is a sectional view of the shoe management apparatus according to the embodiment of the present disclosure, which extends into boots.

FIG. 1 is a front perspective view of a shoe management apparatus 1 according to one embodiment of the present disclosure, FIG. 9 is a perspective view of an interior flow channel 40 of the shoe management apparatus 1 according to the embodiment of the present disclosure, and FIG. 10 is a sectional view of the shoe management apparatus according to the embodiment of the present disclosure, which extends into boots 320.

As shown in FIG. 1, FIG. 9 and FIG. 10, the shoe management apparatus 1 according to the embodiment may dry or sterilize shoes 300 and may have various functions related to management of the shoes 300, such as removal of foreign substances from insoles of the shoes 300 and the like. Foreign substances may include germs, viruses, dirt, and other particles known to be present on or in shoes.

The shoe management apparatus 1 according to the embodiment includes at least one of a casing 10, a receiving portion 50, a first supply portion 90, a second supply portion 180, a third supply portion 200, a rotation-restricting portion 220, a height measurement unit 230, and a controller 240.

The controller 240, and various embodiments described herein may be implemented in a computer-readable medium using, for example, software, hardware, or some combination thereof. For example, the embodiments described herein may be implemented within one or more of Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, other electronic units designed to perform the functions described herein, or a selective combination thereof. In some cases, such embodiments are implemented by the controller. That is, the controller is a hardware-embedded processor executing the appropriate algorithms (e.g., flowcharts) for performing the described functions and thus has sufficient structure. Also, the embodiments such as procedures and functions may be implemented together with separate software modules each of which performs at least one of functions and operations. The software codes can be implemented with a software application written in any suitable programming language. Also, the software codes can be stored in the memory and executed by the controller, thus making the controller a type of special purpose controller specifically configured to carry out the described functions and algorithms. Thus, the components shown in the drawings have sufficient structure to implement the appropriate algorithms for performing the described functions.

Casing

The casing 10 may be realized in various shapes so long as the casing 10 includes an electric compartment 20 for supplying a fluid for drying the shoes 300. According to one embodiment, the casing 10 may include at least one of the electric compartment 20, a water supply portion 30, a water recovery tray 32, a casing body 34, and an interior flow channel 40.

The electric compartment 20 constitutes a lower portion of the casing 10. The electric compartment 20 is provided with a steam generator 24 and a main blower 22. The steam generator 24 is a device for supplying sterilization steam to the first supply portion 90. The steam generator 24 generates steam by heating water supplied thereto. Steam generated by the steam generator 24 may be supplied to the shoes 300, thereby reducing time for sterilization and deodorization of the shoes 300.

The main blower 22 is connected to the steam generator 24 and delivers the steam from the steam generator 24 to the first supply portion 90 through the interior flow channel 40 inside the casing 10. The main blower 22 is provided therein with a fan and a motor to supply steam or air to the first supply portion 90 through the interior flow channel inside the casing 10.

The casing 10 is provided with the water supply portion 30, which supplies water to the steam generator 24. The water supply portion 30 has a tank shape for storing water and is detachably provided to a casing body 34.

Water generated from steam sprayed into the receiving portion 50 is collected by the water recovery tray 32. The water recovery tray 32 has a tank shape for storing water collected from the receiving portion 50 and is detachably provided to (i.e., connected to) the casing body 34.

The interior flow channel 40 (FIG. 9) is a passage connecting the electric compartment 20 to the first supply portion 90 such that a fluid having passed through the electric compartment 20 flows to the first supply portion 90 along the interior flow channel 40. The interior flow channel 40 defines a passage inside the casing body 34, which constitutes a body of the casing 10. The interior flow channel 40 is disposed between an outer surface of the casing body 34 and an inner surface of the casing body 34 to form a passage through which air and/or steam flows.

Accordingly, in the electric compartment 20, a fluid supplied to the interior flow channel 40 may be supplied into the shoes 300 through the first supply portion 90. In addition, the fluid supplied from the electric compartment 20 to the interior flow channel 40 is supplied into the shoes 300 after sequentially passing through the first supply portion 90, the second supply portion 180, and the third supply portion 200.

Receiving Portion

The receiving portion 50 is disposed inside the casing 10 and defines a receiving space for receiving the shoes 300 inside the receiving portion 50. The receiving portion 50 has a box shape open at a front side thereof and may be realized in various shapes so long as the receiving portion 50 can support the first supply portion 90. According to the embodiment, the receiving portion 50 may include at least one of an upper surface 60, a receiving space 64, side surfaces 66, a foothold portion 70, and a rear surface 80.

The upper surface 60 of the receiving portion 50 is disposed at an upper side of the receiving space 64 and is provided with the first supply portion 90. The upper surface 60 of the receiving portion 50 has a plate shape disposed in a horizontal direction or at an acute angle with respect to the horizontal direction. The upper surface 60 is formed with movement holes 62 in which the first supply portion 90 is moved. According to the embodiment, a pair of first supply portions 90 is provided in each receiving portion 50. Accordingly, the upper surface 60 is provided with two movement holes 62 having an elongated shape.

The side surfaces 66 are disposed at opposite sides under the upper surface 60 and extend in a vertical direction and the vertical direction is perpendicular to the horizontal direction. The upper surface 60 is connected to the side surfaces 66 to form an angled C shape open downwards.

The foothold portion 70 is disposed below the upper surface 60 and may be realized in various shapes so long as the foothold portion 70 can store foreign substances falling from the shoes 300. According to one embodiment, the foothold portion 70 may include a support foothold 76 provided/disposed to a lower surface of the receiving portion 50 and a foldable foothold 72 disposed at an upper side of the support foothold 76 to be folded or unfolded.

A support foothold 76 is formed on an upper side thereof with multiple through-holes and has an interior space for storing foreign substances falling from the shoes 300.

The foldable foothold 72 may be disposed above the support foothold 76. Drying and cleaning of low-height shoes 300, such as sneakers 310 and the like, may be performed with the shoes 300 placed on each of the support foothold 76 and the foldable foothold 72.

High-height shoes 300, such as boots 320, which have a higher height than sneakers 310 may be placed on the support foothold 76, with the foldable foothold 72 folded. According to one embodiment, the foldable foothold 72 includes the stationary foothold 73 securely disposed inside the receiving portion 50 and a rotatable foothold 74 rotatably provided to the stationary foothold 73.

The stationary foothold 73 may be disposed in the horizontal direction and the rotatable foothold 74 may be rotated to adjoin an upper side of the stationary foothold 73. In addition, the rotatable foothold 74 may be unfolded to be parallel to the stationary foothold 73, as shown in FIG. 10. Each of the stationary foothold 73 and the rotatable foothold 74 is formed on the upper side thereof with multiple through-holes and has a space for storing foreign substances that fall from the shoes 300.

Since the foothold portion 70 is disposed under the shoes 300, the foreign substances falling from the shoes 300 are stored in the foothold portion 70 and do not fall onto other shoes 300 disposed below the shoes 300, thereby preventing contamination of the other shoes 300.

The rear surface 80 is disposed at the rear side of the receiving space 64 and has a plate shape extending in the vertical direction. The rear surface 80 may be disposed to adjoin or face the interior flow channel 40 of the casing 10. Further, the rear surface 80 may further include an air passage hole 82 and a fan member 84.

The air passage hole 82 is formed in a slit shape on the rear surface 80. Accordingly, some of the fluid flowing to the first supply portion 90 through the interior flow channel 40 may flow into the receiving space 64 through the air passage hole 82.

Further, the fan member 84 may be disposed at the rear side of the air passage hole 82 to force flow of the fluid. By operation of the fan member 84, some of the fluid flowing upwards along the interior flow channel 40 flows into the receiving space 64 through the air passage hole 82.

The fan member 84 provided to the interior flow channel 40 serves to forcibly blow the fluid into the receiving portion 50 through the air passage hole 82. In addition, the fan member 84 forces air or steam flowing along the interior flow channel 40 to flow into the receiving portion 50.

First Supply Portion

Figure 2:
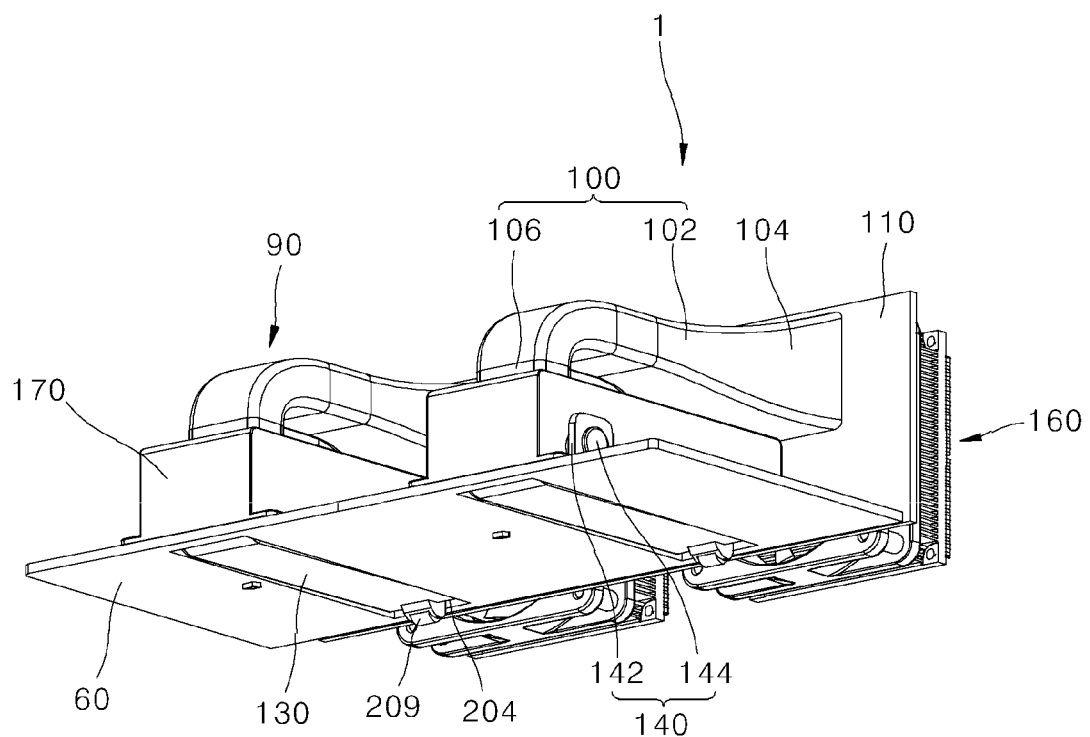
FIG. 2 is a perspective view of a rotatable duct rotated upwards in the shoe management apparatus according to the embodiment of the present disclosure.
Figure 3:
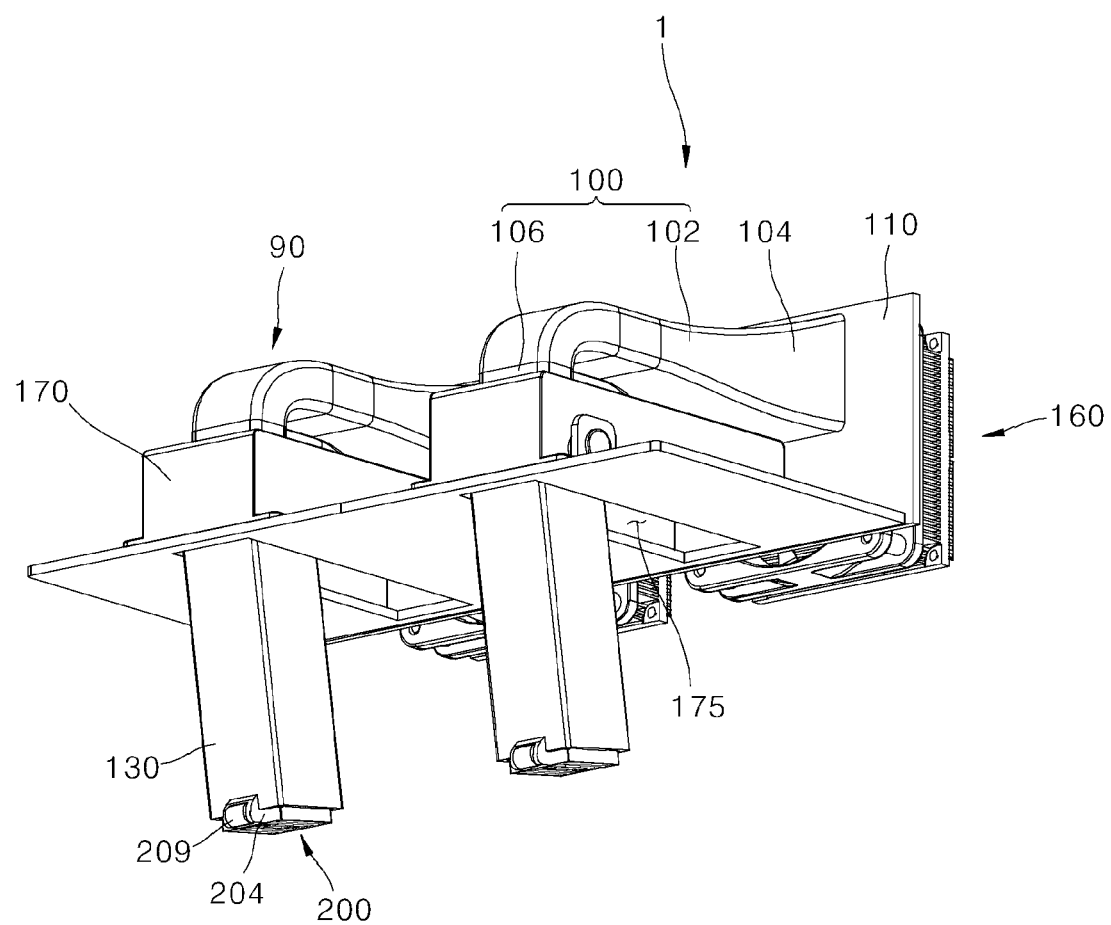
FIG. 3 is a perspective view of the rotatable duct bent downwards in the shoe management apparatus according to the embodiment of the present disclosure.
Figure 4:
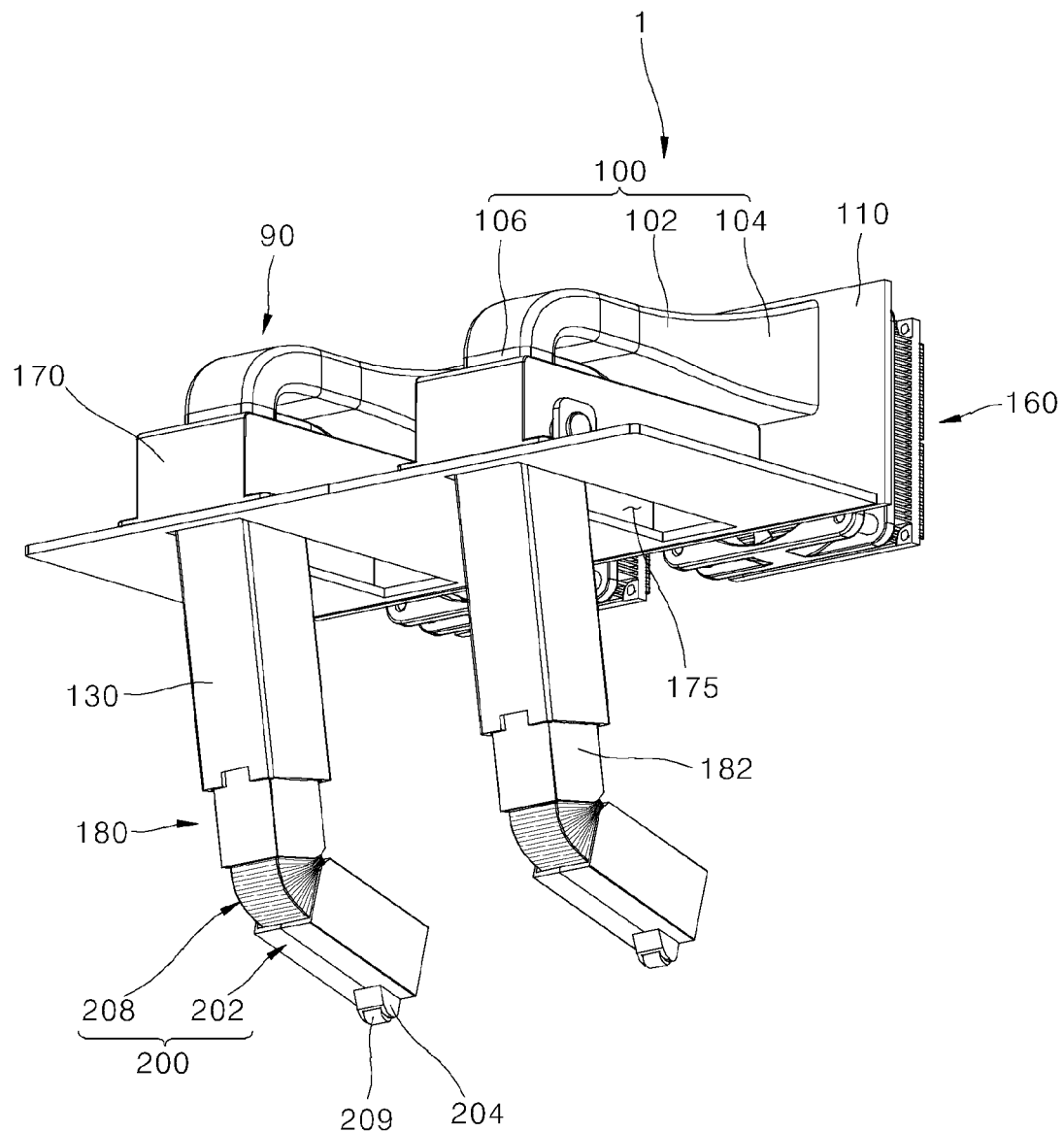
FIG. 4 is a perspective view of a second supply portion and a third supply portion extending to a lower side of the lower duct in the shoe management apparatus according to the embodiment of the present disclosure.
Figure 5:
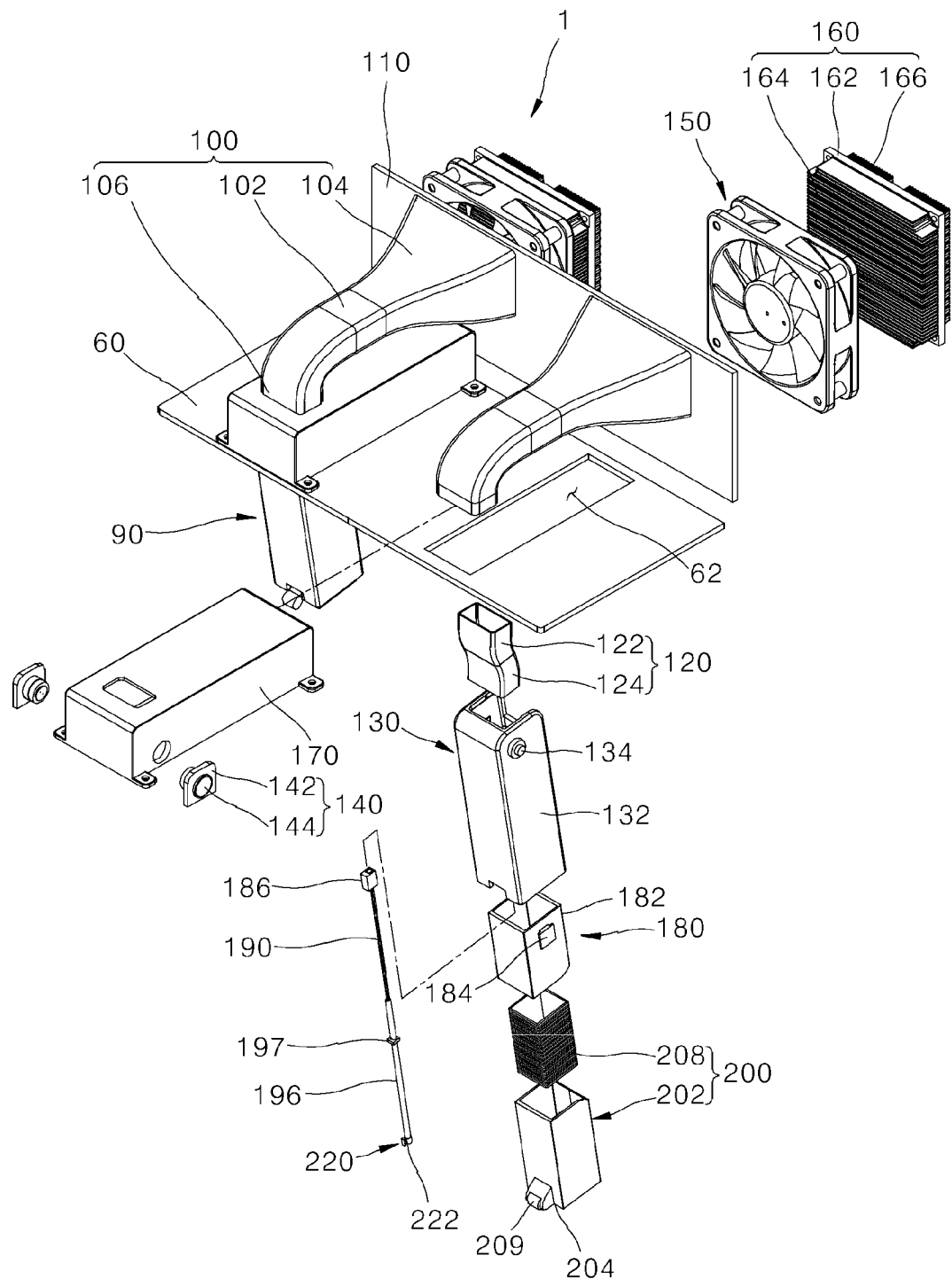
FIG. 5 is an exploded perspective view of the shoe management apparatus according to the embodiment of the present disclosure.

FIG. 2 is a perspective view of a rotatable duct 130 rotated upwards in the shoe management apparatus according to the embodiment of the present disclosure, FIG. 3 is a perspective view of the rotatable duct 130 rotated downwards in the shoe management apparatus according to the embodiment of the present disclosure, FIG. 4 is a perspective view of the second supply portion 180 and the third supply portion 200 extending to a lower side of a lower duct 202 in the shoe management apparatus according to the embodiment of the present disclosure, and FIG. 5 is an exploded perspective view of the shoe management apparatus 1 according to the embodiment of the present disclosure.

As shown in FIG. 2 to FIG. 5, the first supply portion 90 is disposed at an upper side of the receiving portion 50 and is provided with ducts guiding flow of air. In addition, the first supply portion 90 is provided with ducts extending into the receiving space 64 through various ways including rotation. According to the embodiment, the first supply portion 90 allows rotation of the ducts guiding the flow of air therein and guides air supplied from the electric compartment 20 towards the interior of the receiving portion 50.

Only when the shoes 300 are placed inside the receiving portion 50, the first supply portion 90 may be operated to allow the ducts to move into the receiving portion 50 such that air can be supplied into the shoes 300. After drying of the shoes placed in the receiving portion 50 is finished, the first supply portion 90 is returned to an initial location, thereby facilitating removal of the shoes 300 from the receiving portion 50.

According to one embodiment, the first supply portion 90 may include at least one of a stationary duct 100, a duct bracket 110, a flexible duct 120, a rotatable duct 130, a first driver 140, a blower 150, and a heat exchanger 160.

Since the first supply portion 90 is disposed inside the receiving portion 50 before or after drying of the shoes 300 is performed, the shoes 300 are prevented from interfering with other components upon placement of the shoes 300 in the receiving portion 50 or upon removal of the shoes from the receiving portion 50, thereby improving user convenience.

The first supply portion 90 is rotated to be disposed in a bent/angled shape towards the interior of the receiving portion 50, thereby reducing time and costs for drying the shoes 300 through increase in flow rate of air supplied to the shoes 300.

Stationary Duct

The stationary duct 100 is disposed at the upper side of the receiving portion 50 and is provided with ducts guiding the flow of air. The stationary duct 100 is disposed at the upper side of the receiving space 64 and is restricted in movement (e.g., is fixed in place and is not deformable or has minimal deformation). According to one embodiment, the stationary duct 100 includes a first duct 102 and a second duct 106.

The first duct 102 is disposed next to the blower/fan 150 and extends in the horizontal direction. In addition, the second duct 106 is bent/angled downwards from a distal end of the first duct 102 and is connected to the flexible duct 120. Further, the first duct 102 is provided with an enlarged duct 104 in which an inner duct channel has a cross-sectional area gradually increasing from the second duct 106 towards the blower 150. The enlarged duct 104 has an inner curved surface. The enlarged duct 104 may have a bulge shape (i.e., a flared shaped or widening shape) and is disposed such that the cross-sectional area of the inner duct channel gradually increases towards the blower 150.

As a result, air flowing into the first duct 102 through the blower 150 is gradually collected while passing through the enlarged duct 104. As a result, the flow rate of the air flowing from the enlarged duct 104 towards the second duct 106 increases, since the cross-sectional area decreases from the enlarged duct 104 to the second duct 106. Further, the blower 150 is operated to increase the flow rate of the air supplied into the stationary duct 100, thereby reducing time for drying the shoes 300.

The stationary duct 100 may have an inverted L-shape and is angled/bent along a curved shape of the second duct 106, thereby suppressing an increase in friction between an inner surface of the stationary duct 100 and air sequentially passing through the first duct 102 and the second duct 106.

Duct Bracket

The duct bracket 110 supports the first ducts 102 of the stationary ducts 100. The duct bracket 110 may be secured to at least one of the receiving portion 50 and the casing 10. According to one embodiment, the duct bracket 110 has a plate shape standing upright and supports a distal end of the first duct 102. Accordingly, the duct bracket 110 extends in the horizontal direction and is connected to two first ducts 102 separated from each other in the horizontal direction. Further, the duct bracket 110 may be disposed between the blower 150 and the stationary ducts 100.

Flexible Duct

Figure 6:
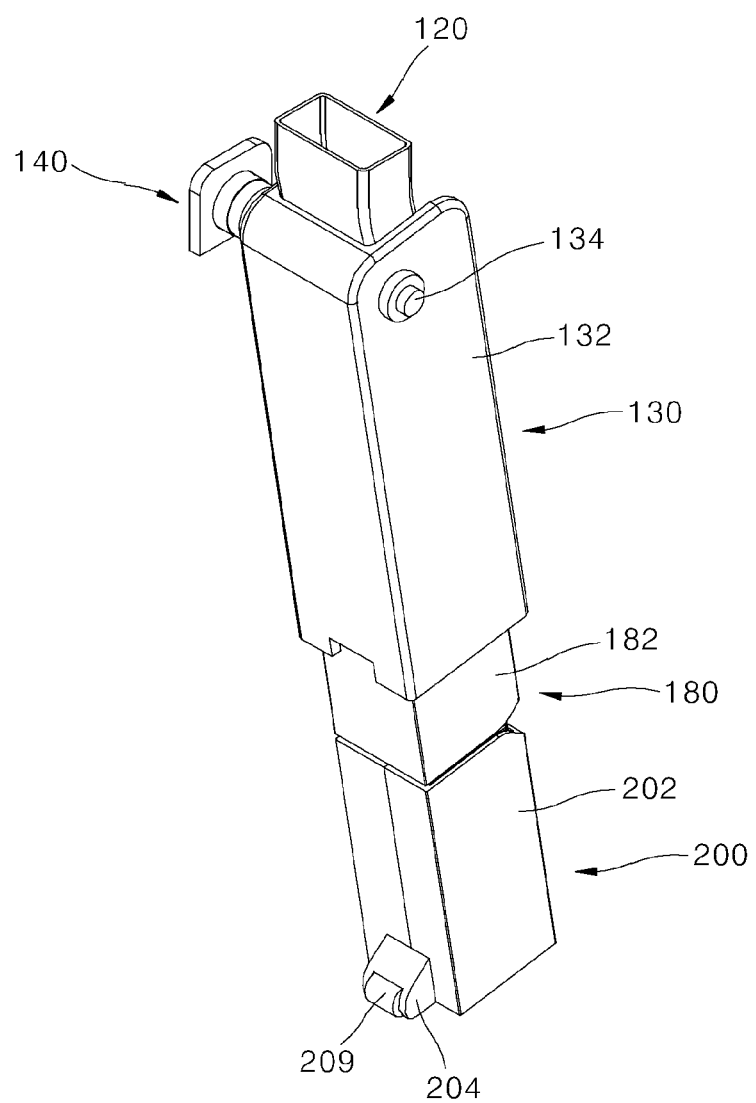
FIG. 6 is a perspective view of the second supply portion connected to the lower duct in the shoe management apparatus according to the embodiment of the present disclosure.
Figure 7:
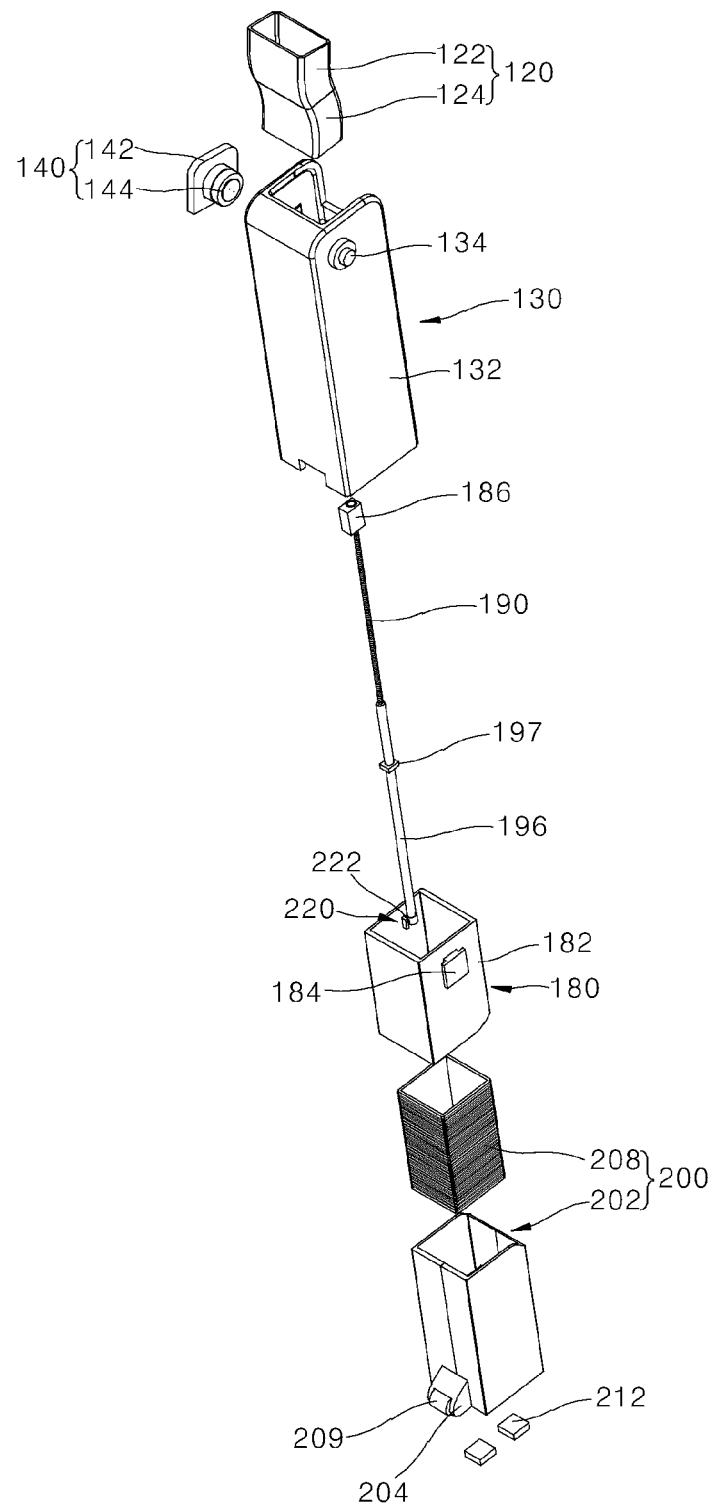
FIG. 7 is an exploded perspective view of the rotatable duct, the second supply portion and the third supply portion in the shoe management apparatus according to the embodiment of the present disclosure.

FIG. 6 is a perspective view of the second supply portion 180 connected to the lower duct 130 in the shoe management apparatus according to the embodiment of the present disclosure and FIG. 7 is an exploded perspective view of the rotatable duct 130, the second supply portion 180 and the third supply portion 200 in the shoe management apparatus according to the embodiment of the present disclosure.

Referring to FIG. 6 and FIG. 7, the flexible duct 120 is connected to the stationary duct 100 and may be realized in various shapes so long as the shape of the stationary duct 100 can be changed through rotation thereof. According to the present disclosure, the flexible duct 120 is connected at an upper side thereof to the stationary duct 100 and extends such that a lower side of the flexible duct 120 is disposed inside the rotatable duct 130. Accordingly, the flexible duct guides the air received through the stationary duct 100 to flow into the rotatable duct 130.

The flexible duct 120 defines a duct channel having multiple bent shapes such that air flows into the rotatable duct 130 along a zigzag shape through the flexible duct 120. According to one embodiment, the flexible duct 120 includes a first flexible tube 122 connected to the stationary duct 100, first flexible tube 122 including one surface having a concave shape and a second flexible tube 124 connected to the first flexible tube 122, the second flexible tube 124 including one surface having a convex shape.

The first flexible tube 122 is connected to a lower end of the second duct 106 and forms a curved shape having a wave shape facing downwards. The second flexible tube 124 is connected to a lower end of the first flexible tube 122 and forms a curved shape having a wave shape facing downwards. The shape of each of the first flexible tube 122 and the second flexible tube 124 is changed corresponding to the location of the rotatable duct 130 (i.e., depending on location/angle of rotation of the rotatable duct 130).

Inner channels of the first flexible tube 122 and the second flexible tube 124 have the same cross-sectional area, and air flowing into the first duct 102 through the enlarged duct 104 flows towards the flexible duct 120 through the second duct 106.

The flexible duct 120 may be disposed in a curved shape corresponding to the wave shape and may be modified into various shapes, for example, a spiral shape or a twisted shape. Accordingly, air supplied into the rotatable duct 130 through the flexible duct 120 may form an active air stream.

The air supplied into the rotatable duct 130 through the flexible duct 120 flows in a zigzag shape, thereby enabling uniform drying of the shoes 300.

The flexible duct 120 may include silicone or rubber and may be selected from various materials so long as the material can be deformed by external force.

Rotatable Duct

The rotatable duct 130 is connected to the flexible duct 120 and may be realized in various shapes so long as the rotatable duct 130 is disposed outside the second supply portion 180. The rotatable duct 130 receives the air supplied through the stationary duct 100 or the flexible duct 120 and may move into the receiving space 64 through rotation or movement in a longitudinal direction thereof.

According to one embodiment, the rotatable duct 130 is connected to the flexible duct 120 and is rotated to move into the receiving space 64. The rotatable duct 130 is rotated through operation of the first driver 140. Specifically, when the receiving space 64 does not receive the shoes 300, the rotatable duct 130 is rotated to an upper side of the receiving space 64. As a result, the rotatable duct 130 is disposed inside a stationary housing 170 through the movement hole 62 formed on the upper surface 60.

When air is to be supplied into the shoes 300, the rotatable duct 130 is rotated through operation of the first driver 140. The rotatable duct 130 is rotated towards the receiving portion 50 through the movement hole 62 to supply air into the shoes 300.

The rotatable duct 130 is rotatably provided to (i.e., rotatably connected/attached to) the stationary housing 170 and is operated in a first mode in which the rotatable duct 130 is rotated towards the interior of the stationary housing 170, and in a second mode in which the rotatable duct 130 is rotated away from the interior of the stationary housing 170 and towards the interior of the receiving space 64.

When the first supply portion 90 is not operated, the first supply portion 90 is stably stored inside the stationary housing 170, thereby improving durability of components.

The rotatable duct 130 is rotatably disposed inside the stationary housing 170 and defines a duct channel open at one side thereof.

According to one embodiment, the rotatable duct 130 includes a rotatable duct body 132 constituting a body of the rotatable duct 130 and having an angled tube shape, and guide grooves 136 formed inside the rotatable duct body 132 in the longitudinal direction of the rotatable duct body 132.

The rotatable duct body 132 is open at opposite sides (i.e., sides opposite one another in an axial or lengthwise direction) thereof such that the flexible duct 120 can be inserted into the rotatable duct body 132 through one side thereof to supply air into the rotatable duct body 132.

In addition, the rotatable duct body 132 is provided at opposite sides thereof with hinge protrusions 134. The hinge protrusions 134 protruding from the rotatable duct body 132 are inserted into grooves formed on an inner surface of the stationary housing 170 to be rotated thereon. The hinge protrusions 134 are formed on the opposite sides of the rotatable duct 130 protruding upwards from the upper surface 60 and rotatably provided to the stationary housing 170 secured to an upper side of the upper surface 60.

The guide grooves 136 extend in the longitudinal direction inside the rotatable duct 130. The rotatable duct 130 is formed with a pair of guide grooves 136 facing each other and parallel to each other. In addition, stopper protrusions 184 provided to the second supply portion 180 described below are linearly guided along the guide grooves 136. In addition, each of the guide grooves 136 is provided at a distal end thereof with a latch step to prevent the stopper protrusions 184 from being separated from the rotatable duct 130 by catching the stopper protrusions 184 at the distal ends of the guide grooves 136. The stopper protrusion 184 is moved along the guide grooves 136, thereby enabling stable linear movement of a duct body 182.

First Driver

The first driver 140 is connected to the rotatable duct 130 and may be selected from various kinds of driving devices capable of supplying power for rotation of the rotatable duct 130. According to one embodiment, the first driver 140 includes a motor bracket 142 secured to the receiving portion 50 or the stationary housing 170 and a drive motor 144 secured to the motor bracket 142 and axially connected to a rotational center of the rotatable duct 130 to rotate the rotatable duct 130.

The drive motor 144 may be directly connected to the rotational center of the rotatable duct 130 such that power of the drive motor 144 is sequentially delivered to a transmission to increase torque and is then delivered to the rotational center of the rotatable duct 130.

The motor bracket 142 is secured to the upper surface 60 of the receiving portion 50 and the drive motor 144 supported by the motor bracket 142 is disposed to pass through a side surface of the stationary housing 170. In addition, since an output shaft of the drive motor 144 is connected to the hinge protrusions 134 of the rotatable duct 130, the rotatable duct 130 including the hinge protrusions 134 is rotated by operation of the drive motor 144.

The drive motor 144 may be a servomotor or a stepper motor and may rotate the rotatable duct 130 in response to a control signal sent from the controller 240.

Blower

The blower 150 is disposed next to the stationary duct 100 and may be realized in various shapes so long as the blower can supply air into the stationary duct 100. According to one embodiment, the blower 150 is provided with a rotatable fan and is disposed at an inlet of the stationary duct 100.

The blower 150 is disposed at a location facing the enlarged duct 104. The blower 150 disposed between the enlarged duct 104 and the interior flow channel 40 increases the flow rate of air flowing in the interior flow channel 40 towards the enlarged duct 104. Operation and rpm of the blower 150 are controlled by the controller 240.

Heat Exchanger

The heat exchanger 160 is disposed next to the blower 150 (e.g., the heat exchanger 160 may be directly contacting/abutting the blower 150) and may be selected from various heat exchangers capable of performing heat exchange with air flowing into the blower 150. According to one embodiment, the heat exchanger 160 performs heat exchange using the Peltier effect. The heat exchanger 160 includes a Peltier device 162, a first heat exchange plate 164, and a second heat exchange plate 166.

The Peltier device 162 uses a phenomenon in which a bonded portion between two different metals is cooled upon conduction of electric current therethrough and may be used as a temperature regulator including a cooler, a heater, and the like. The Peltier device 162 has a plate shape and allows variation in temperature thereof upon supply of electric current thereto. In order to supply air having higher temperature into the shoes 300 than room temperature, the Peltier device 162 heats the first heat exchange plate 164 facing the inlet of the stationary duct 100. When room temperature increases above 30° C. as in summer, the first heat exchange plate 164 may be cooled to reduce the temperature of the dried shoes 300.

The first heat exchange plate 164 is connected to one side of the Peltier device 162 and performs heat exchange with air flowing into the blower 150. According to one embodiment, the first heat exchange plate 164 has a plate shape adjoining the Peltier device 162 and is provided with multiple heat exchangers on a side surface thereof facing the stationary duct 100 to increase an area of heat exchange with air.

Accordingly, a contact area between the first heat exchange plate 164 and air flowing to the stationary duct 100 through the first heat exchange plate 164 is increased, thereby improving efficiency in heat exchange of the heat exchanger 160.

The second heat exchange plate 166 is connected to the other side of the Peltier device 162 and performs heat exchange with air. According to one embodiment, the second heat exchange plate 166 has a plate shape adjoining the Peltier device 162 and is provided with multiple heat exchangers (e.g., fins) on a side surface thereof opposite the first heat exchange plate 164 to increase an area of heat exchange with air.

Accordingly, a contact area between the second heat exchange plate 166 and air passing through the surroundings of the second heat exchange plate 166 is increased, thereby improving efficiency in heat exchange of the heat exchanger 160.

In operation of drying the shoes 300, the heat exchanger 160 is operated to regulate the temperature of air supplied to the shoes 300, thereby reducing time for drying the shoes 300.

Stationary Housing

As shown in FIG. 5, the stationary housing 170 is secured to the receiving portion 50 and has an interior space 175 in which the rotatable duct 130 rotated to the upper side of the receiving portion 50 and the second supply portion 180 are placed. The stationary housing 170 is secured to the receiving portion 50 while surrounding the flexible duct 120. In addition, the stationary housing 170 is open at a lower side thereof and has the interior space 175 in which the rotatable duct 130 rotated to the upper side of the receiving portion 50 is placed.

The interior space 175 of the stationary housing 170 communicates with the movement hole 62 of the upper surface 60. Accordingly, the second supply portion 180 and the third supply portion 200 rotatable together with the rotatable duct 130 may be placed in the interior space 175 of the stationary housing 170.

The stationary housing 170 prevents leakage of air flowing to the upper side of the receiving portion 50 through the movement hole 62 of the receiving portion 50. Further, the stationary housing 170 prevents foreign substances inside the casing 10 from falling into the receiving space 64 through the movement hole 62.

Second Supply Portion

Figure 8:
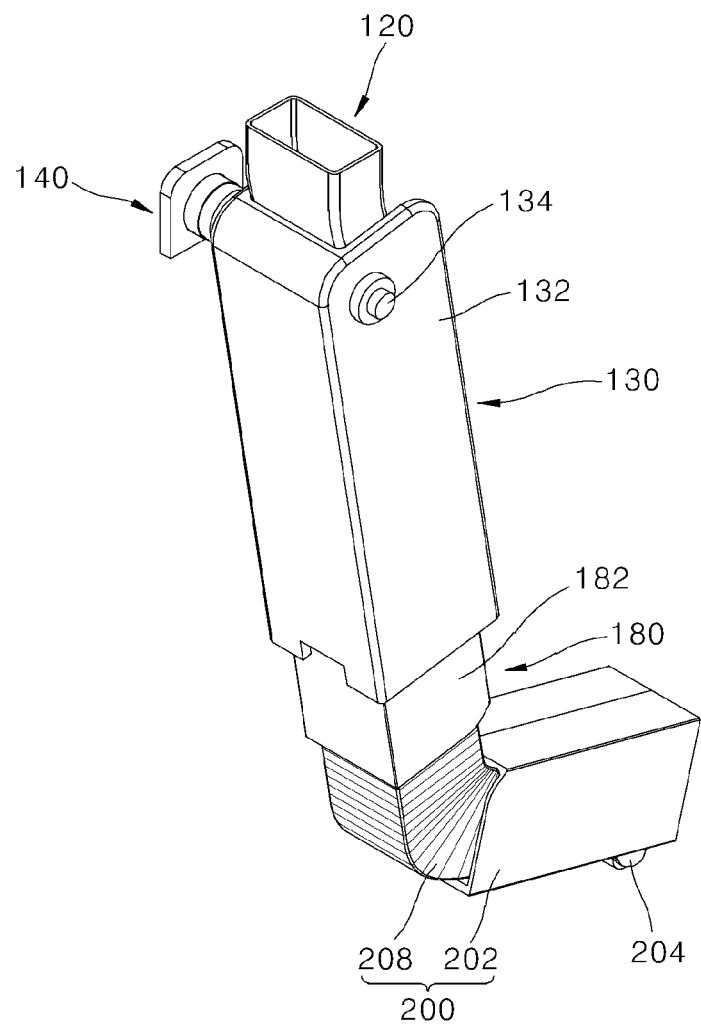
FIG. 8 is a perspective view of a third duct disposed in a bent shape in the shoe management apparatus according to the embodiment of the present disclosure.
Figure 11:
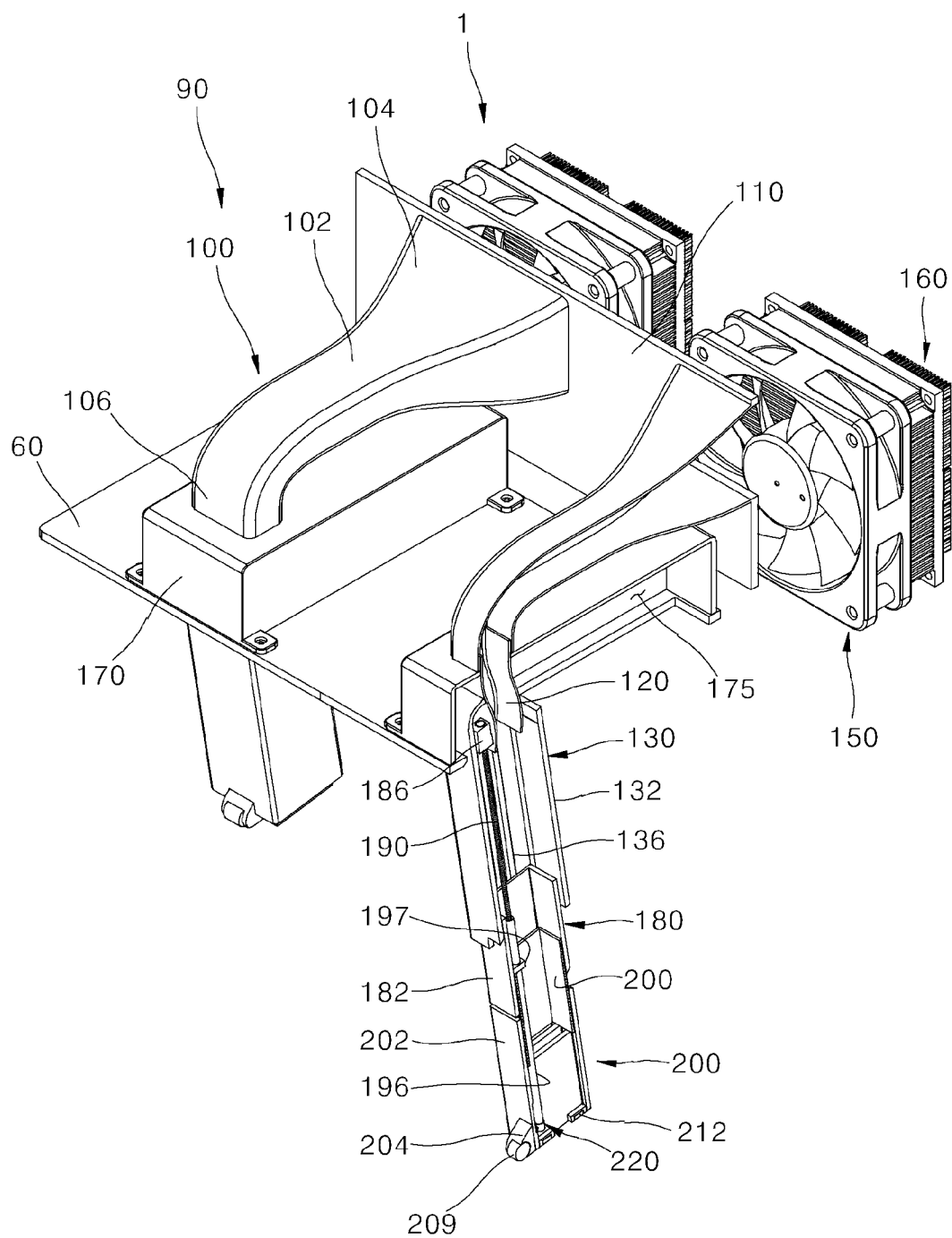
FIG. 11 is a partially sectional perspective view of main components of the shoe management apparatus according to the embodiment of the present disclosure.
Figure 12:
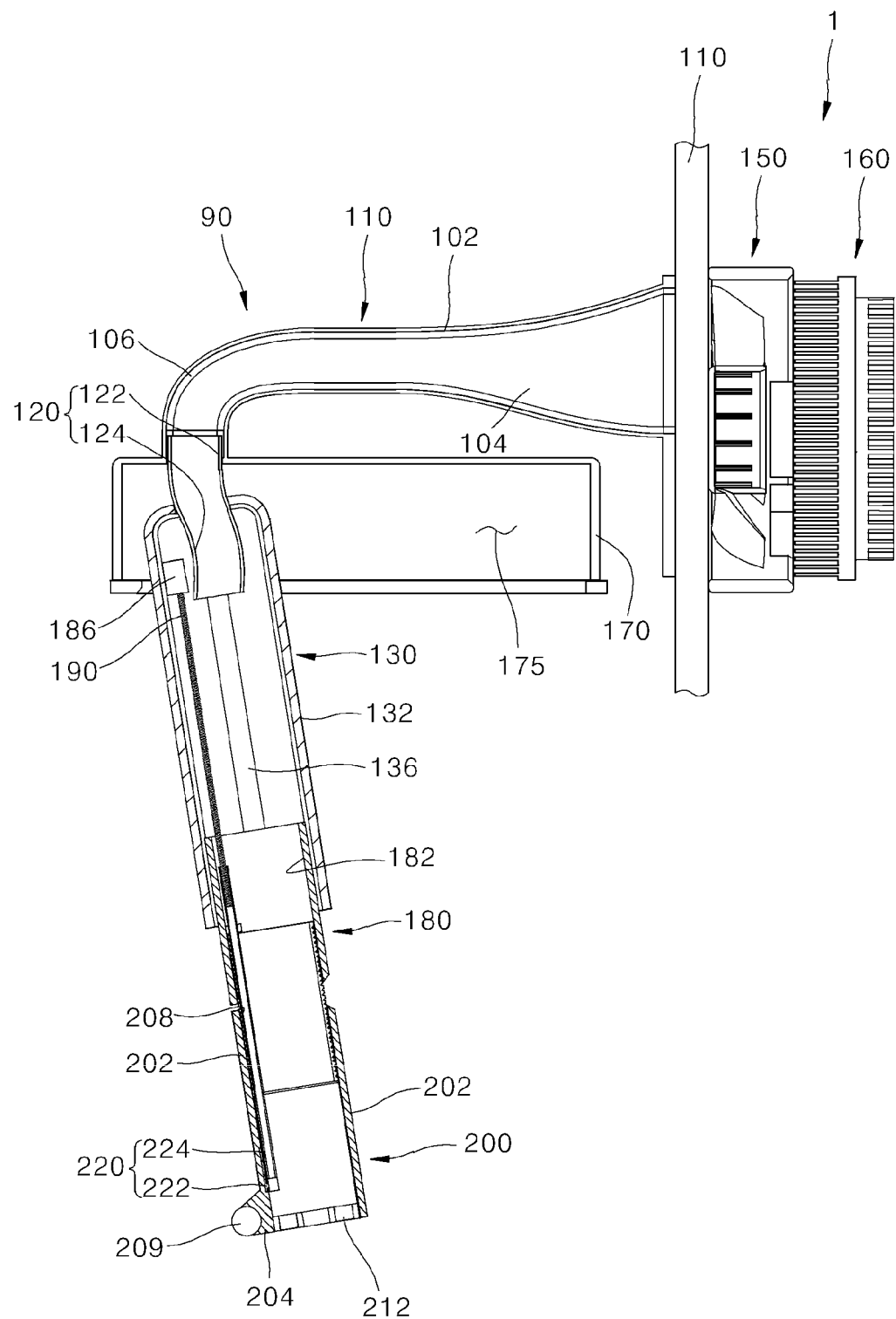
FIG. 12 is a sectional view of the main components of the shoe management apparatus according to the embodiment of the present disclosure.

FIG. 8 is a perspective view of a third duct disposed in a bent shape in the shoe management apparatus according to the embodiment of the present disclosure, FIG. 11 is a partially sectional perspective view of main components of the shoe management apparatus according to the embodiment of the present disclosure, and FIG. 12 is a sectional view of the main components of the shoe management apparatus according to the embodiment of the present disclosure.

As shown in FIG. 8, FIG. 11, and FIG. 12, the second supply portion 180 is disposed inside the first supply portion 90 and may be realized in various shapes so long as the second supply portion 180 protrudes towards a lower side of the first supply portion 90 in the longitudinal direction of the first supply portion 90 to supply air into the shoes 300. The second supply portion 180 is connected to the first supply portion 90 and extends downwards from the first supply portion 90 rotated towards the interior of the receiving portion 50.

As such, since the second supply portion 180 increases the length of a flow channel for supplying air, the second supply portion 180 can easily deliver the air supplied from the first supply portion 90 towards the interior of the shoes 300. The second supply portion 180 is connected to the first supply portion 90 and extends from the first supply portion 90, which is rotated into the receiving portion 50, into the shoes 300. Accordingly, the air supplied to the rotatable duct 130 of the first supply portion 90 flows towards the shoes 300 through the second supply portion 180.

The second supply portion 180 extends to the lower side of the first supply portion 90 to increase the flow rate of the air supplied to the shoes 300, thereby reducing time and costs for drying the shoes 300.

According to one embodiment, the second supply portion 180 includes at least one of the duct body 182, the stopper protrusions 184, a second driver 186, a screw bar 190, and a core member 196.

Duct Body

The duct body 182 is disposed inside the rotatable duct 130 and extends to guide air in a linear direction along the rotatable duct 130. According to the embodiment, the duct body 182 is disposed inside the rotatable duct 130 and has an angled tube shape open at both sides thereof.

According to one embodiment, the duct body 182 extends in the linear direction and has a rectangular flow channel therein.

The duct body 182 moves in the linear direction along the interior of the rotatable duct 130, thereby extending a section guiding flow of the air discharged through the lower side of the rotatable duct 130. Further, the stopper protrusions 184 protruding outwards from the duct body 182 are caught and guided to move in the linear direction by the guide grooves 136 in the rotatable duct 130. The stopper protrusions 184 protrude from opposite sides of the duct body 182 and are rotatably inserted into the stationary housing 170.

The second supply portion 180 includes the stopper protrusions 184 protruding from the outer surface of the duct body 182. The first supply portion 90 includes the guide grooves 136 extending in the linear direction on an inner surface of the rotatable duct 130 facing the duct body 182. Accordingly, linear movement of the stopper protrusions 184 is guided along the guide grooves 136.

Since the second driver 186 is connected to the first supply portion 90 and generates rotational force, the second driver 186 may be selected from various kinds of driving devices capable of moving at least one of the second supply portion 180 and the third supply portion 200 in the linear direction of the first supply portion 90. According to one embodiment, the second driver 186 may employ a motor that generates rotational force upon application of electric energy thereto.

The second driver 186 is secured inside the rotatable duct 130 and has an output shaft connected to the screw bar 190. The screw bar 190 is rotated by rotational force from the second driver 186. When the rotatable duct 130 is rotated downwards, the rotatable duct 130 is disposed in an inclined direction to have an acute angle with respect to the vertical direction or a vertical line.

According to one embodiment, the second supply portion 180 is slantedly lowered (i.e., lowered while being positioned at an angle with respect to the shoe 300) towards an insole 302 of the shoe 300 at an acute angle with respect to the insole 302. Accordingly, after passing through the second supply portion 180 or after sequentially passing through the second supply portion 180 and the third supply portion 200, an air stream supplied into the shoes 300 slantedly moves (e.g., moves at an angle) into the shoes 300 while adjoining the insoles 302, thereby reducing time and cost for drying the shoes 300.

Since the second supply portion 180 is slantedly lowered towards the insole 302 of the shoe 300 at an acute angle with respect to the insole 302 thereof, the third supply portion 200 can be easily bent/rotated while slantedly adjoining the insole 302 (i.e., contacting the insole 302 while being positioned at an angle with respect to the shoe 300), thereby improving operation reliability of the third supply portion 200.

The third supply portion 200 is connected to a lower side of the second supply portion 180 and can be easily bent while slantedly adjoining (i.e., adjoining or contacting at an angle) the insole 302, thereby further facilitating the flow of air supplied into the shoe 300.

Figure 13:
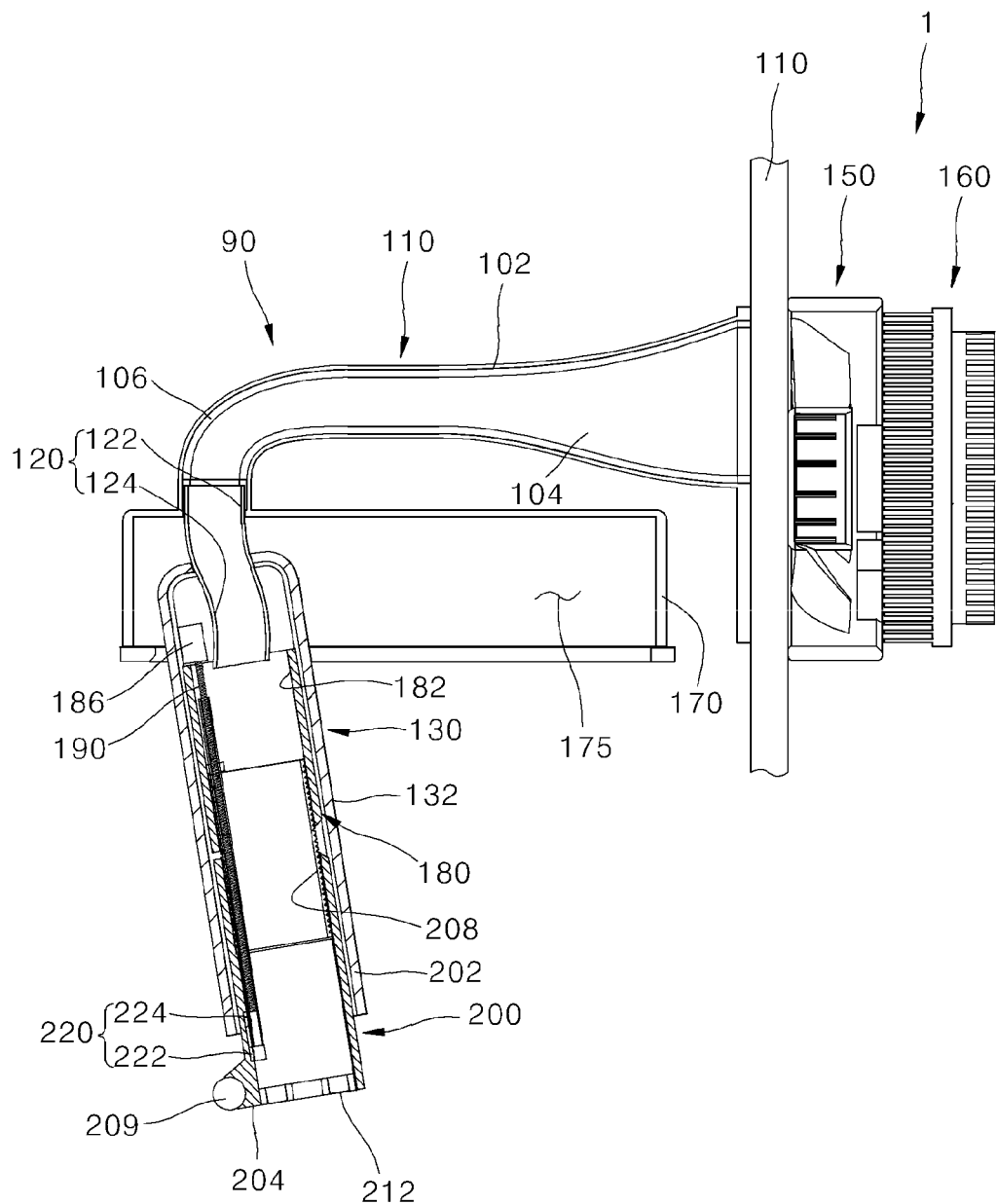
FIG. 13 is a sectional view of the second supply portion and the third supply portion moved upwards in the shoe management apparatus according to the embodiment of the present disclosure.
Figure 14:
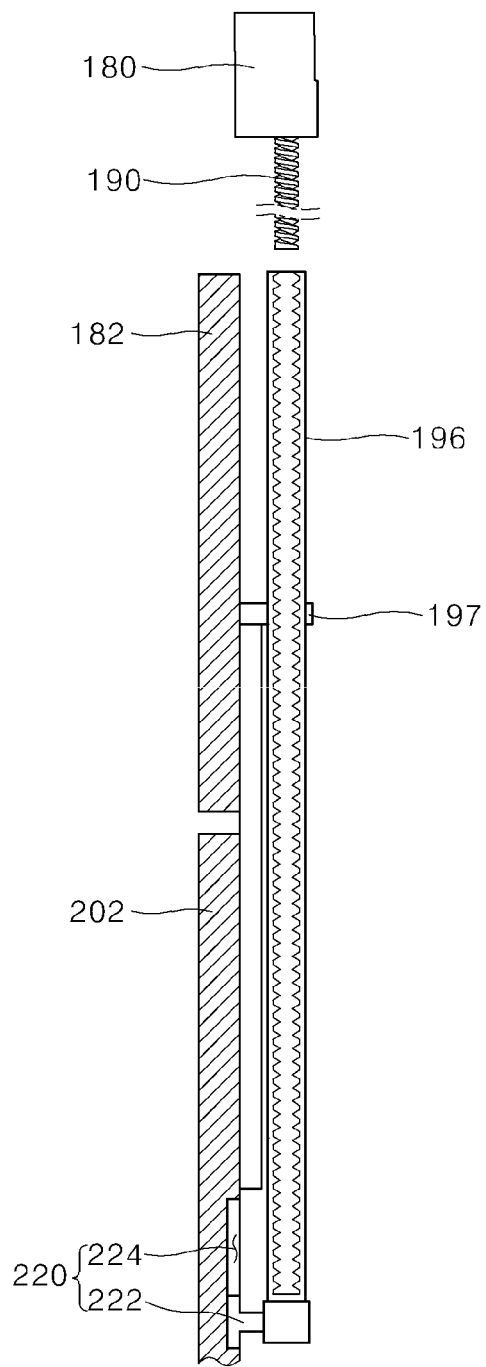
FIG. 14 is a perspective view of a screw bar and a core member separated from each other in the shoe management apparatus according to the embodiment of the present disclosure.
Figure 15:
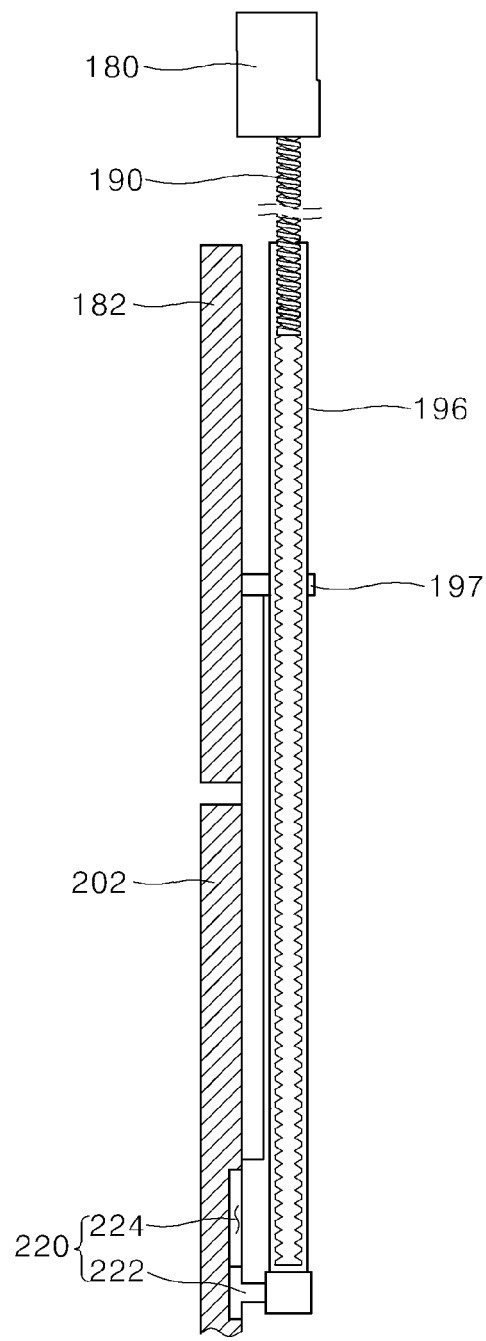
FIG. 15 is a perspective view of the screw bar and the core member coupled to each other in the shoe management apparatus according to the embodiment of the present disclosure.
Figure 16:
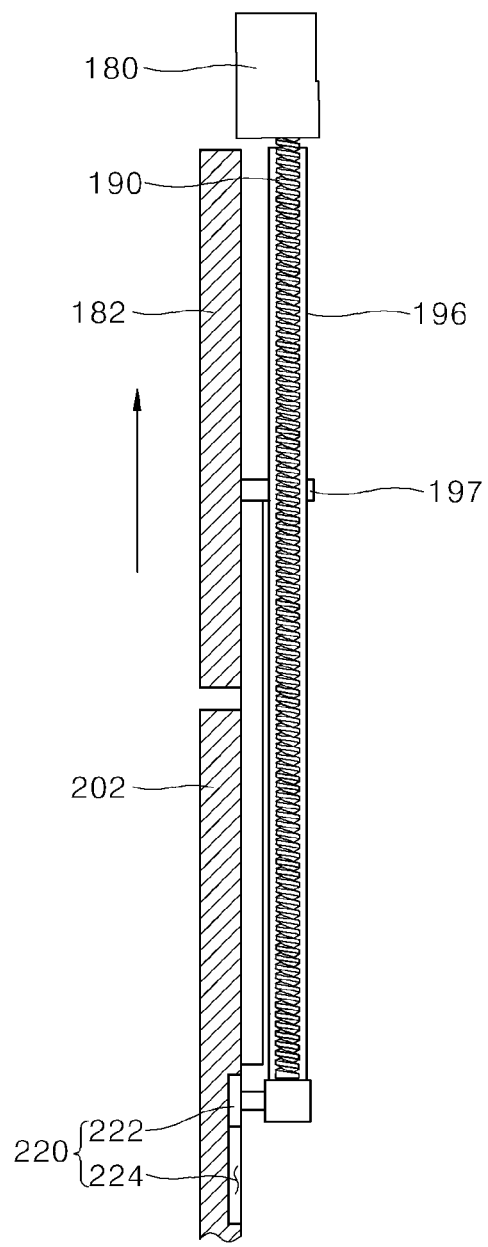
FIG. 16 is a perspective view of the core member moved upwards along the screw bar in the shoe management apparatus according to the embodiment of the present disclosure.

FIG. 13 is a sectional view of the second supply portion 180 and the third supply portion 200 moved upwards in the shoe management apparatus according to the embodiment, FIG. 14 is a perspective view of the screw bar 190 and the core member 196 separated from each other in the shoe management apparatus according to the embodiment, FIG. 15 is a perspective view of the screw bar 190 and the core member 196 coupled to each other in the shoe management apparatus according to the embodiment, and FIG. 16 is a perspective view of the core member 196 moved upwards along the screw bar 190 in the shoe management apparatus according to the embodiment.

Referring to FIG. 13 to FIG. 16, the second driver 186 is secured to the rotatable duct 130 and the screw bar 190 extends downwards along the rotatable duct 130. The screw bar 190 has a bar shape extending in the longitudinal direction of the rotatable duct 130 and is formed on an outer surface thereof with an outer gear having a male-thread shape.

The screw bar 190 is disposed inside the rotatable duct 130 and the duct body 182 and is rotated clockwise or counterclockwise by operation of the second driver 186.

The core member 196 is connected to an outer surface of the screw bar 190 and may be realized in various shapes so long as the core member 196 can be moved in the longitudinal direction along the screw bar 190 by rotation of the screw bar 190.

According to one embodiment, the core member 196 has a tube shape having an inner gear corresponding to the outer gear of the screw bar 190. Further, the core member 196 is linearly moved along the screw bar 190 by rotation of the screw bar 190 and is connected to the duct body 182 or a lower duct 202 disposed at a lower side of the duct body 182.

The core member 196 may be directly connected to the duct body 182 or the lower duct 202 or may be connected thereto via a separate member, as needed.

According to one embodiment, the core member 196 has a flexible tube shape and is formed on the inner surface thereof with the inner gear having a female-thread shape, which engages with the outer gear of the screw bar 190, in order to be inserted into and coupled to the screw bar 190.

The stationary support 197 is connected to the core member 196 and the duct body 182. Accordingly, the duct body 182, the stationary support 197 and the core member 196 are disposed inside the rotatable duct 130 and moved in the longitudinal direction of the rotatable duct 130.

The stationary support 197 is connected to an upper portion of the core member 196 and is disposed to surround the core member 196. Since a protrusion protruding from the stationary support 197 is secured inside the duct body 182, the stationary support 197 is moved together with the core member 196 and the duct body 182.

Third Supply Portion

The third supply portion 200 is disposed next to the second supply portion 180 and is bent towards a front side of the shoe 300 while adjoining the insole 302 of the shoe 300. The third supply portion 200 may be realized in various shapes so long as the third supply portion 200 can change a discharge direction of air flowing downwards along the second supply portion 180 such that the air can flow towards the front side of the shoe 300.

The third supply portion 200 may be moved together with the duct body 182 by operation of the second driver 186 and may define a flow channel bent into the shoes 300 while adjoining the insole 302 of the shoe 300. In addition, when the third supply portion 200 is separated from the shoe 300, the bent flow channel is changed into a linear flow channel.

The third supply portion 200 is bent/angled towards the front side of the shoe 300 while adjoining the insole of the shoe 300, thereby reducing time and cost for drying the shoes 300.

According to one embodiment, the third supply portion 200 may include at least one of the lower duct 202, a deformable duct 208, a roller member 209, and a sterilizer 212.

Lower Duct

Figure 17:
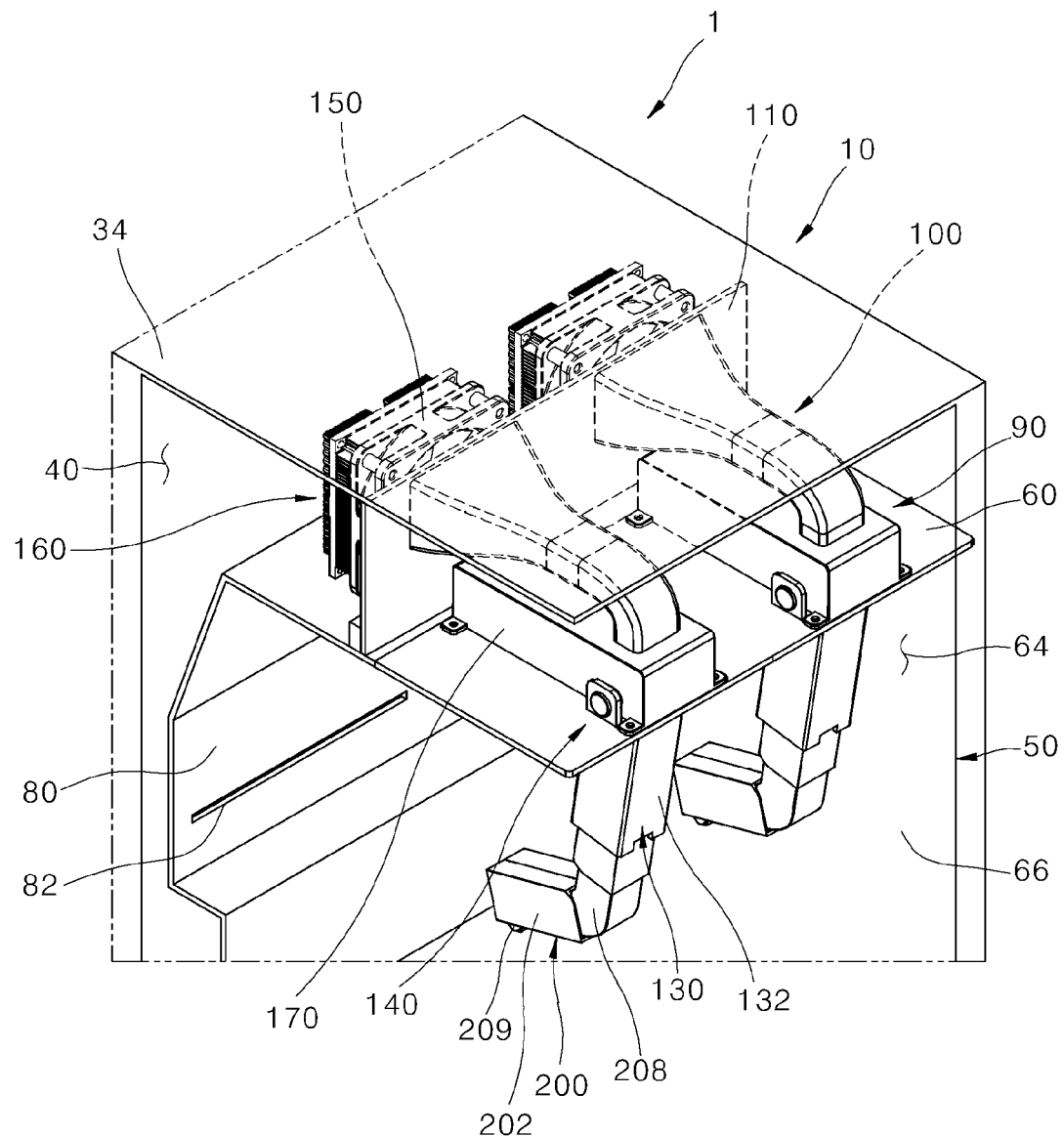
FIG. 17 is a perspective view of a second driver and a third driver in a rotatable duct extending into a receiving portion in the shoe management apparatus according to the embodiment of the present disclosure.
Figure 18:
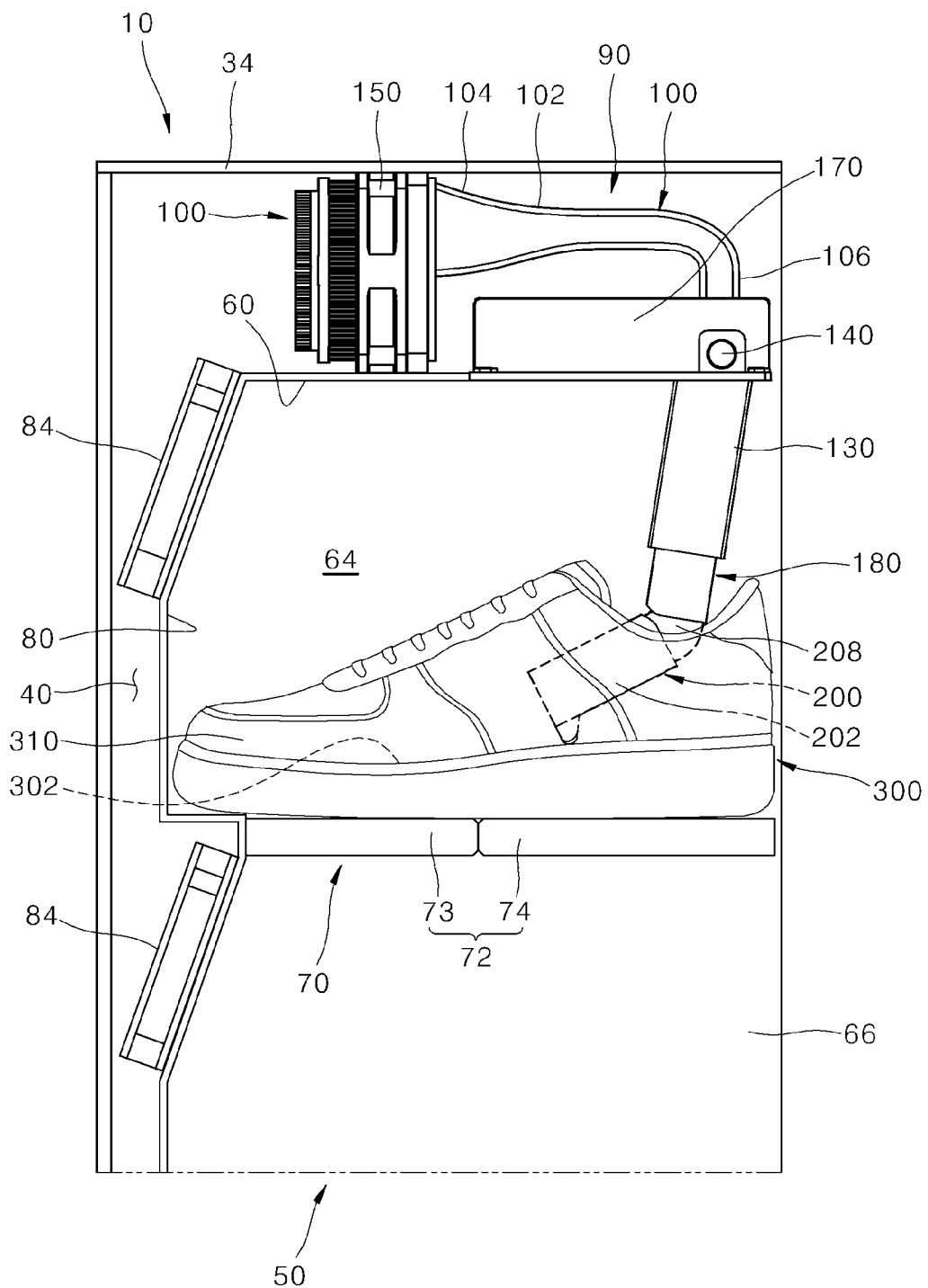
FIG. 18 is a sectional view of the third supply portion bent while adjoining an insole of a shoe in the shoe management apparatus according to the embodiment of the present disclosure.
Figure 19:
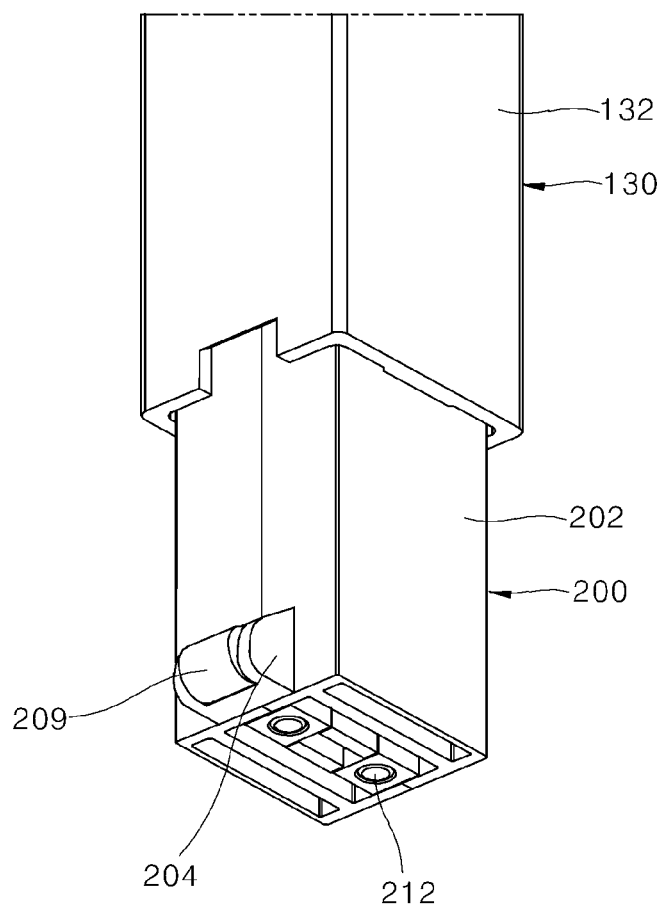
FIG. 19 is a perspective view of a distal end of the third supply portion in the shoe management apparatus according to the embodiment of the present disclosure.

FIG. 17 is a perspective view of the second driver 186 and a third driver extending in the rotatable duct 130 extending into the receiving portion 50 in the shoe management apparatus according to the embodiment, FIG. 18 is a sectional view of the third supply portion 200 bent while adjoining the insole 302 of the shoe 300 in the shoe management apparatus according to the embodiment, and FIG. 19 is a perspective view of a distal end of the third supply portion 200 in the shoe management apparatus according to the embodiment.

Referring to FIG. 17 to FIG. 19, the lower duct 202 is disposed at the lower side of the second supply portion 180 and is bent towards the front side of the shoe 300 while adjoining the insole 302 of the shoe 300. The lower duct 202 of the third supply portion 200 is disposed together with the duct body 182 of the second supply portion 180 inside the rotatable duct 130 of the first supply portion 90.

The lower duct 202 has a rectangular tube shape and is open at opposite sides thereof. The lower duct 202 is lowered towards the insole 302 of the shoe 300 at an acute angle with respect to the insole 302 thereof. When the lower duct 202 is lowered in a direction perpendicular to the insole 302, the air discharged from the lower duct 202 is highly likely to move above the insole 302 after adjoining the insole 302. Accordingly, when the rotatable duct 130 is rotated towards the shoe 300, an imaginary line extending from the rotatable duct 130 has an acute angle with respect to a horizontal line. Further, an imaginary line extending from the second supply portion 180 and the third supply portion 200 protruding downwards from the rotatable duct 130 has an acute angle with respect to the horizontal line.

Accordingly, with the second supply portion 180 and the third supply portion 200 placed inside the first supply portion 90, the air discharged through a lower side of the first supply portion 90 can easily flows towards the front side of the shoe 300 while slantedly colliding the insole 302 of the shoe 300.

Alternatively, with the second supply portion 180 and the third supply portion 200 extending to the lower side of the first supply portion 90, the roller member 209 provided to the third supply portion 200 is moved while adjoining the insole 302 of the shoe 300, thereby allowing the third supply portion 200 to be deformed in a bent shape. Air can be supplied towards the front sides of the shoes through the third supply portion 200 deformed in a bent shape.

Deformable Duct

The deformable duct 208 connects the lower duct 202 to the second supply portion 180 and may be realized in various shapes so long as the deformable duct 208 can be deformed by external force. According to one embodiment, the deformable duct 208 is a corrugated pipe having elasticity and is deformed into a bent shape by external force. Further, the deformable duct 208 is returned to a linear tube shape upon removal of the external force therefrom.

Even when the location of the lower duct 202 is changed, the shape of the deformable duct 208 is changed to allow air to be smoothly supplied to the lower duct 202, thereby improving operation reliability.

Roller Member

The roller member 209 is rotatably disposed at a lower side of the lower duct 202 and is rotated while adjoining the insole 302 of the shoe 300, thereby guiding a bending operation of the third supply portion 200 while reducing friction of the third supply portion 200.

The roller member 209 is rotatably provided to a roller bracket 204 protruding from the lower duct 202 towards a counter lining of the shoe 300. The roller bracket 204 is disposed on a side surface of the lower duct 202 facing the rear surface 80 of the receiving portion 50 and the roller member 209 is rotatably provided to the roller bracket 204.

Since the roller member 209 is rotated while adjoining the insole of the shoe 300, the third supply portion 200 can be easily bent inside the shoe 300, thereby improving operation reliability.

Sterilizer

The sterilizer 212 is disposed at the lower side of the lower duct 202 and emits light for sterilization towards the interior of the shoes 300. The sterilizer 212 may employ a light emitting diode emitting UVC and may be selected from various kinds of light sources for emitting light for sterilization.

The sterilizer 212 is disposed at the lower side of the third supply portion 200 and sterilizes the interior of the shoes 300 through irradiation with light for sterilization. Operation of the sterilizer 212 is controlled by the controller 240.

As the sterilizer 212 is operated to sterilize the shoes 300 with light for sterilization, it is possible to prevent propagation of pathogens via the shoes 300.

Rotation-Restricting Portion

The rotation-restricting portion 220 may be realized in various shapes so long as the rotation-restricting portion 220 can restricts rotation of the core member 196 while allowing linear movement of the core member 196 along the lower duct 202. According to one embodiment, the rotation-restricting portion 220 may include a rotation-restricting protrusion 222 and a rotation-restricting groove 224.

The rotation-restricting protrusion 222 may be realized in various shapes so long as the rotation-restricting protrusion 222 can connect the core member 196 to the lower duct 202. The core member 196 is connected to an inner surface of the lower duct 202 through the rotation-restricting protrusion 222. The rotation-restricting protrusion 222 is disposed outside a lower portion of the core member 196 and is secured to the core member 196 to move together with the core member 196 in the longitudinal direction of the lower duct 202.

The rotation-restricting protrusion 222 disposed inside the lower duct 202 is inserted into the rotation-restricting groove 224 formed on the inner surface of the lower duct 202. The rotation-restricting protrusion 222 is inserted into the rotation-restricting groove 224 to restrict rotation of the core member 196 while allowing linear movement of the core member 196 in the longitudinal direction of the lower duct 202.

The rotation-restricting protrusion 222 is disposed in a ring shape surrounding a lower side of the core member 196 and the rotation-restricting protrusion 222 is inserted into the rotation-restricting groove 224 formed inside the lower duct 202.

The rotation-restricting groove 224 is formed on the inner surface of the lower duct 202 in the longitudinal direction of the lower duct 202. The rotation-restricting protrusion 222 is inserted into the rotation-restricting groove 224 to slide in the rotation-restricting groove 224, and, when the lower duct 202 disposed at the lower side of the rotatable duct 130 is disposed in a bent shape, the rotation-restricting protrusion 222 connected to the core member 196 moves along the rotation-restricting groove 224.

The rotation-restricting groove 224 has a length set in consideration of the length of the rotation-restricting protrusion 222 that slides when the lower duct 202 moves in a bent shape.

Height Measurement Unit

Figure 23:
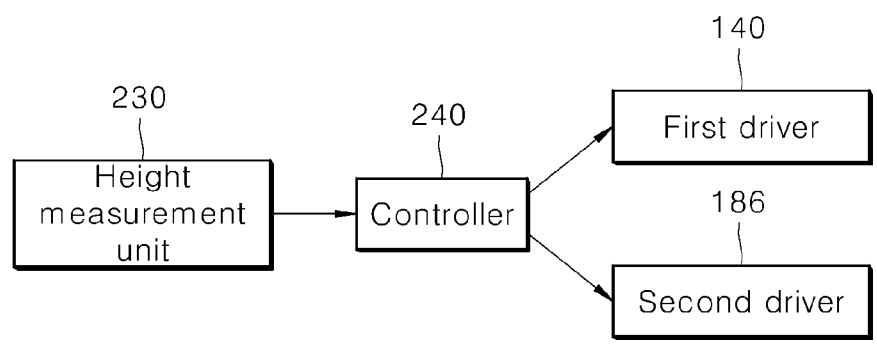
FIG. 23 is a block diagram of the shoe management apparatus according to the embodiment of the present disclosure.

FIG. 23 is a block diagram of the shoe management apparatus 1 according to the embodiment of the present disclosure.

As shown in FIG. 1 and FIG. 23, the height measurement unit 230 is disposed inside the receiving portion 50 and may be realized in various ways so long as the height measurement unit 230 can measure the height of the shoes received in the receiving portion 50 to send a measured value to the controller 240. According to one embodiment, the height measurement unit 230 is provided with multiple measurement sensors 232 disposed along the side surface 66 of the receiving portion 50 in the vertical direction.

The controller 240 may operate only the first supply portion 90 based on the measured value sent from the height measurement unit 230. Alternatively, the controller 240 may sequentially operate the first supply portion 90 and the second supply portion 180 based on the measured value sent from the height measurement unit 230.

According to the present disclosure, the shoe management apparatus 1 is provided with the foldable foothold 72 and the height measurement unit 230 to allow low-height shoes 300, such as sneakers 310, to be dried together with high-height shoes 300, such as boots 320, having a greater height than the sneakers 310, thereby reducing installation costs of the shoe management apparatus 1.

Sequential Operation of First Supply Portion, Second Supply Portion and Third Supply Portion Operation of the shoe management apparatus 1 according to the embodiment will be described in detail with reference to the accompanying drawings.

Figure 20:
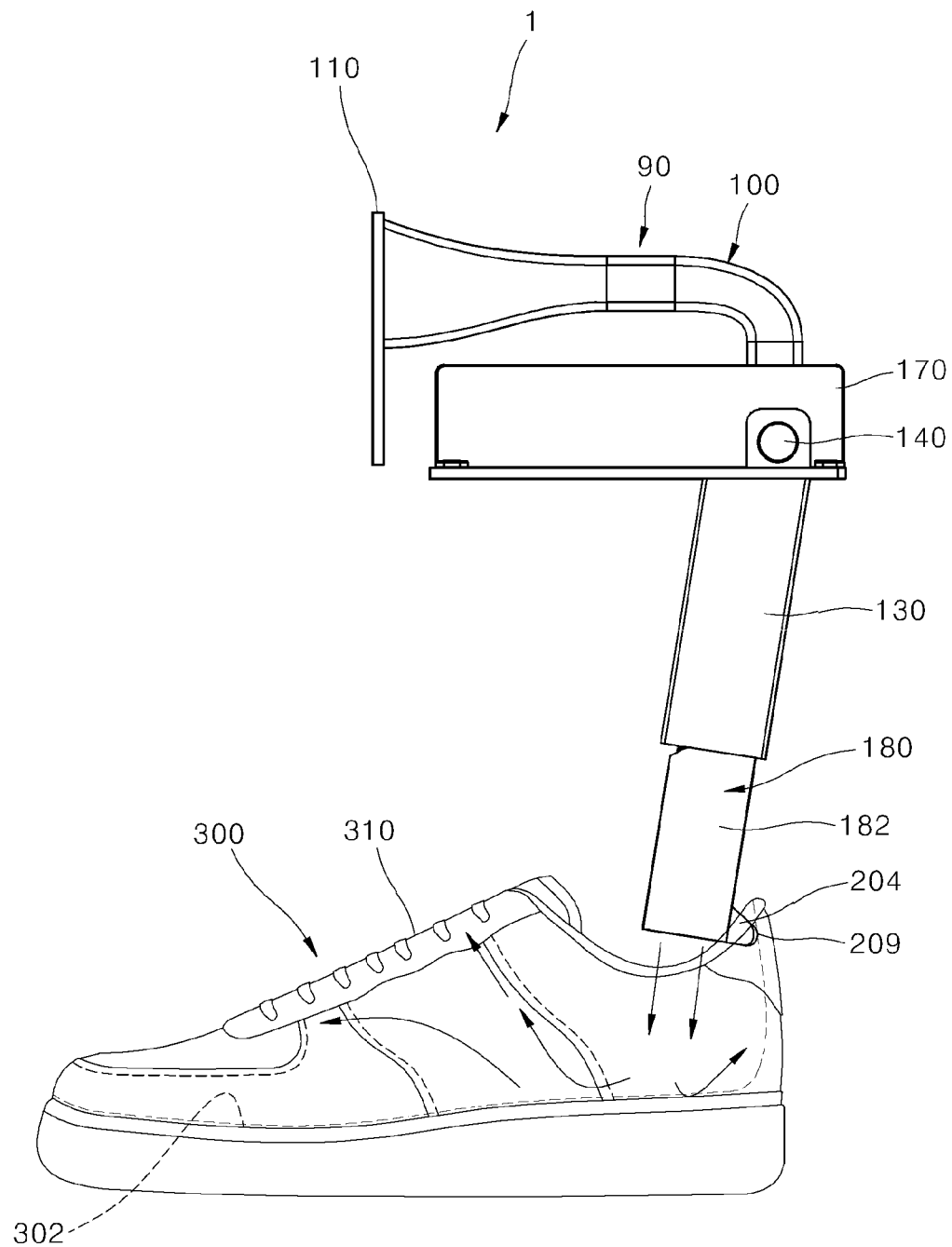
FIG. 20 is a side view of the second supply portion extending to a lower side of the first supply portion in the shoe management apparatus according to the embodiment of the present disclosure.
Figure 21:
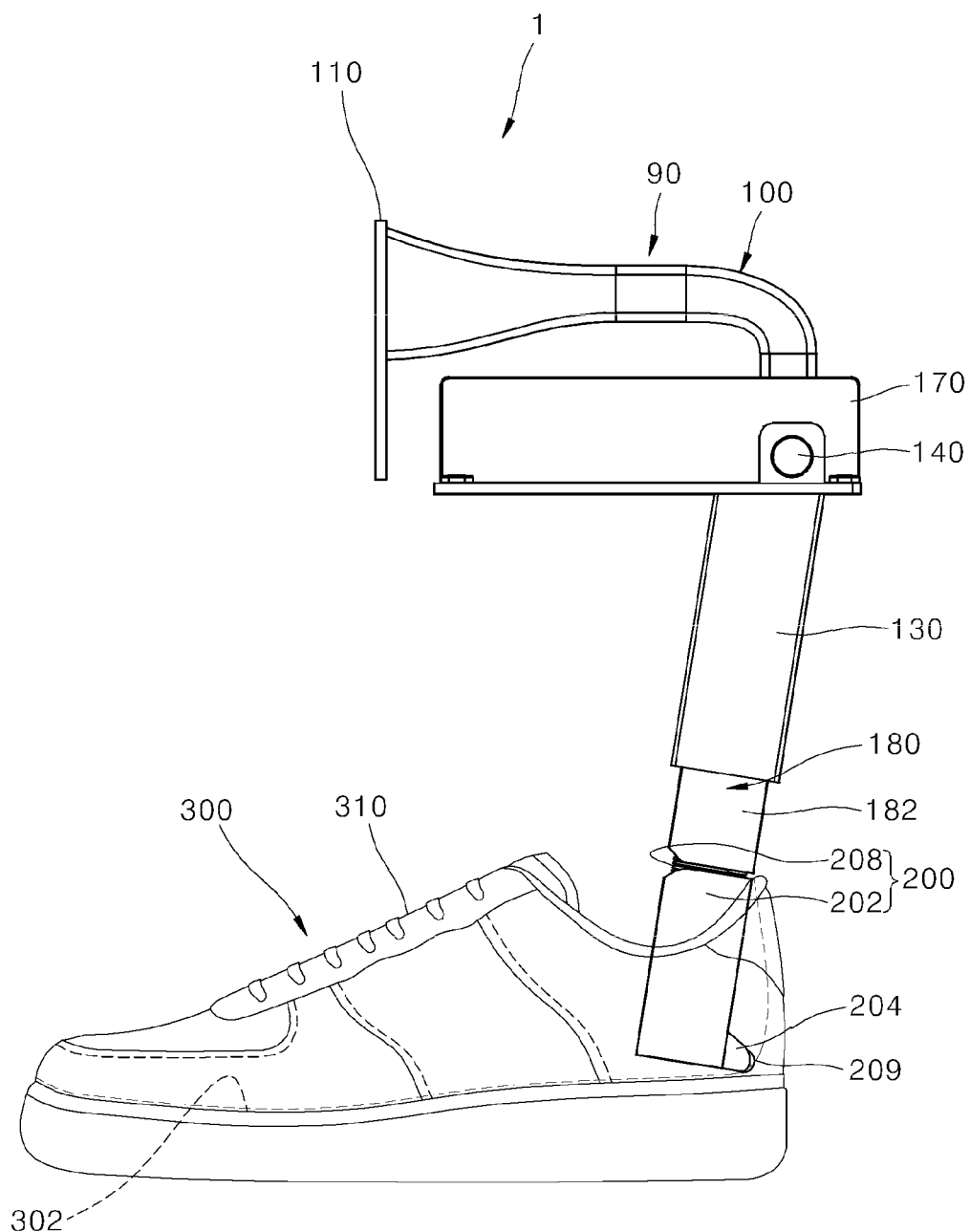
FIG. 21 is a side view of the third supply portion adjoining the insole of the shoe in the shoe management apparatus according to the embodiment of the present disclosure.
Figure 22:
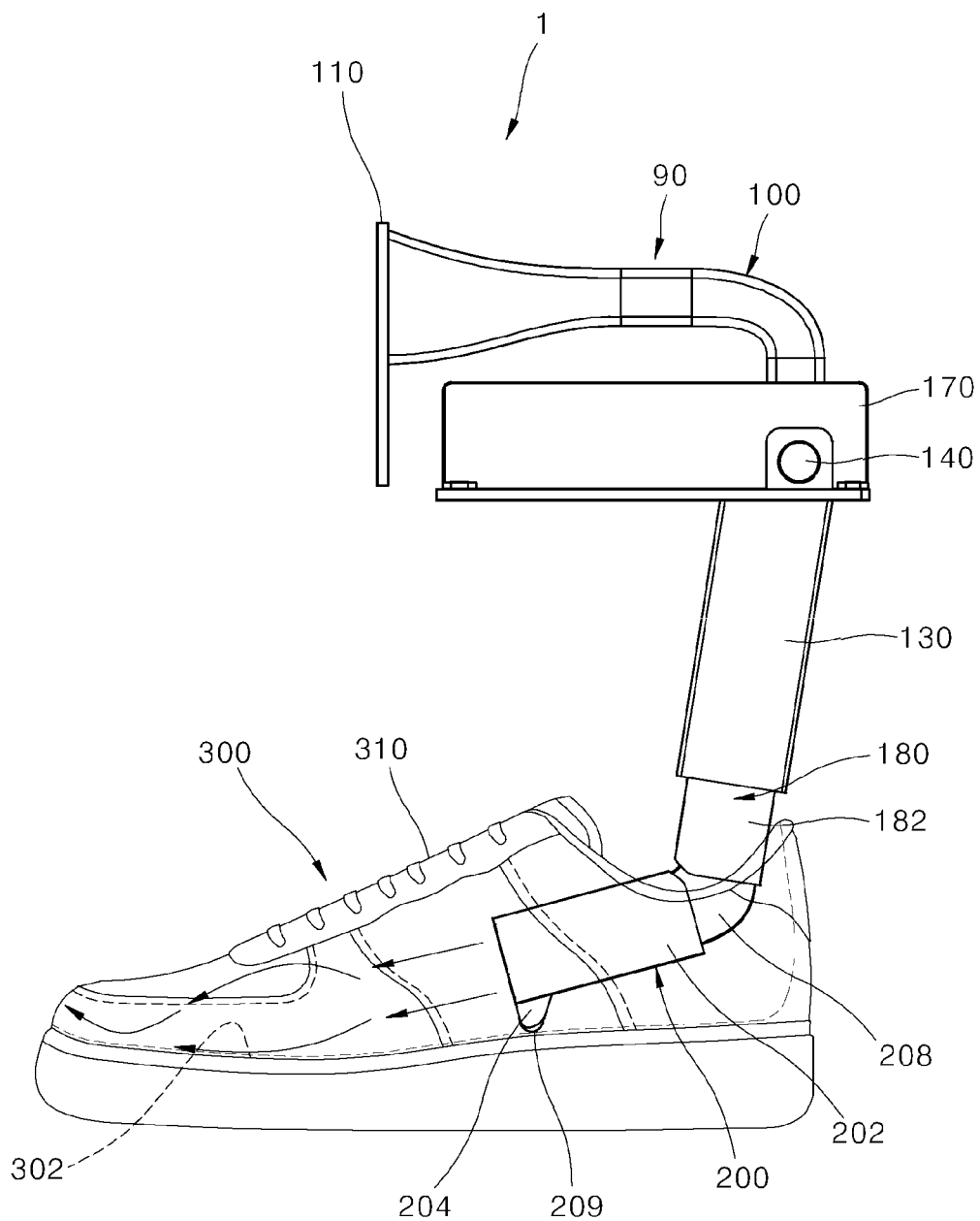
FIG. 22 is a side view of the third supply portion bent to a front side of the shoe in the shoe management apparatus according to the embodiment of the present disclosure.

FIG. 20 is a side view of the second supply portion 180 extending to the lower side of the first supply portion 90 in the shoe management apparatus according to the embodiment of the present disclosure, FIG. 21 is a side view of the third supply portion 200 adjoining the insole of the shoe 300 in the shoe management apparatus according to the embodiment of the present disclosure, and FIG. 22 is a side view of the third supply portion 200 bent to a front side of the shoe 300 in the shoe management apparatus according to the embodiment of the present disclosure.

As shown in FIG. 3 and FIG. 20 to FIG. 22, in a state in which the receiving portion 50 does not receive the shoes 300, the rotatable duct 130 is rotated to the upper side of the receiving portion 50 to be placed in the interior space 175 of the stationary housing 170 at an upper side of the upper surface 60. Accordingly, by placing the shoes 300 in the receiving portion 50, the shoes 300 are prevented from colliding against the rotatable duct 130.

As shown in FIG. 18, when the shoes 300 are placed in the receiving portion 50, the measurement sensors 232 of the height measurement unit 230 detect the shoes 300 and send a detection result to the controller 240. In addition, since the height measurement unit 230 is provided with the multiple measurement sensors 232 in the vertical direction, the measurement sensors 232 measure the heights of the shoes 300 and send the detection results to the controller 240.

The controller 240 determines whether the first driver 140 is operated alone or together with the second driver 186 and/or the third driver based on the measured heights of the shoes 300.

When the controller 240 operates the first driver 140, the rotatable duct 130 is rotated by rotational force from the first driver 140. The rotatable duct 130 disposed inside the stationary housing 170 is rotated to a lower side of the upper surface 60 and stopped where air can be supplied into the shoes 300 therethrough.

In addition, the controller 240 operates the second driver 186 to allow the duct body 182 to protrude from the lower side of the rotatable duct 130. The screw bar 190 is rotated by rotational force from the second driver 186 to allow the core member 196 engaging with the screw bar 190 through the gears to move downwards along the screw bar 190.

The core member 196 has the threads formed on the hollow inner surface thereof which engages with the threads formed on the outer surface of the screw bar 190 and the core member 196 is connected to the stationary support 197 such that rotation of the core member 196 can be restricted. The core member 196 is secured to the inner surface of the duct body 182 through the stationary support 197 and the duct body 182 is disposed inside the rotatable duct 130, thereby restricting rotation of the duct body 182.

When the duct body 182 is moved downwards through downward movement of the core member 196, the lower duct 202 disposed at the lower side of the duct body 182 is connected to the lower side of the core member 196 via the rotation-restricting portion 220. Accordingly, the duct body 182 and the lower duct 202 are moved downwards through downward movement of the core member 196.

On the other hand, air is supplied to the first supply portion 90 through the interior flow channel 40 inside the casing 10. Air flowing through the interior flow channel 40 may or may not contain steam.

Air not containing steam is supplied through the main blower 22 of the electric compartment 20. Air discharged from the main blower 22 flows upwards through the interior flow channel 40 inside the casing 10.

Some of the air flowing through the interior flow channel 40 is supplied to the receiving portion 50 through the air passage hole 82 formed on the rear surface 80 to dry the shoes 300. By operation of the fan member 84 disposed at the rear side of the rear surface 80, some of the air flowing upwards along the interior flow channel 40 can be easily supplied to the air passage hole 82.

The air supplied to the first supply portion 90 through the interior flow channel 40 is supplied into the shoes 300 and dries the shoes 300.

When steam containing air is supplied to the interior flow channel 40, steam generated from the steam generator 24 flows upwards together with air discharged from the main blower 22 to the receiving portion 50 after passing through the interior flow channel 40.

The air flowing into the first supply portion 90 through the interior flow channel 40 is supplied to the interior of the shoes 300 and used for various purposes, such as sterilization or deodorization of the shoes 300.

The air supplied through the interior flow channel 40 is heated or cooled to a predetermined temperature while passing through the heat exchanger 160 and is then moved into the stationary duct 100 through the blower 150. Then, air entering the rotatable duct 130 through the flexible duct 120 connected to the stationary duct 100 flows to the lower side of the rotatable duct 130 while forming a wave-shaped air stream corresponding to the shape of the flexible duct 120.

The air flowing to the lower side of the lower duct 202 is supplied into the shoes 300 and dries the interiors of the shoes 300 by sequentially passing through the duct body 182, the deformable duct 208 and the lower duct 202.

The air supplied into the receiving portion 50 through the air passage hole 82 of the receiving portion 50 dries outer surfaces of the shoes 300.

Here, the duct body 182 extends to the lower side of the rotatable duct 130 and the deformable duct 208 and the lower duct 202 are sequentially connected to the lower side of the duct body 182 to form a tube shape extending in the longitudinal direction. Accordingly, air discharged through the first supply portion 90, the second supply portion 180 and the third supply portion 200 forms an air stream in a linear direction towards the interior of the shoes 300.

When the controller 240 operates the second driver 186 to further move the duct body 182 downwards, the roller member 209 disposed at the lower side of the third supply portion 200 adjoins the insole 302 of the shoe 300 and the third supply portion 200 defines a flow channel in a bent shape.

The third supply portion 200 is slantedly lowered towards the insole 302 of the shoe 300 such that the lower duct 202 is rotated at a predetermined angle about the deformable duct 208 to allow the roller member 209 to adjoin the insole 302. The length of the deformable duct 208 is increased and the rotation-restricting protrusion 222 is moved along the rotation-restricting groove 224 through rotation of the lower duct 202.

The core member 196 has a function of lifting or lowering the second supply portion 180 and the third supply portion 200 and a function of maintaining the shape of the third supply portion 200 disposed in a bent shape.

Accordingly, air flowing to the duct body 182 of the second supply portion 180 through the first supply portion 90 is supplied into the shoes 300 and dries the shoes 300 after sequentially passing through the deformable duct 208 and the lower duct 202.

The third supply portion 200 defines a flow channel in a bent state, thereby enabling uniform and rapid drying of the interiors of the shoes 300.

Further, air to be supplied into the shoes 300 may be realized in various ways, for example, air containing steam or a deodorizing agent. In addition, the sterilizer 212 disposed in the lower duct 202 is operated to sterilize germs inside the shoes 300.

Operation of First Supply Portion Alone

The shoe management apparatus according to the present disclosure may be provided with the first supply portion 90 alone without the second supply portion 180 and the third supply portion 200.

When the shoes 300 are placed in the receiving portion 50, the measurement sensors 232 of the height measurement unit 230 detect the shoes 300 and send a detection result to the controller 240. Since the height measurement unit 230 is provided with the multiple measurement sensors 232 in the vertical direction, the height measurement unit 230 measures the heights of the shoes 300 and sends a measured value to the controller 240.

Based on the measured value of the shoes 300, the controller 240 operates the first driver 140. As a result, the rotatable duct 130 is rotated by rotational force from the first driver 140. The rotatable duct 130 disposed inside the stationary housing 170 is rotated to the interior of the receiving portion 50 and stopped where air can be supplied into the shoes 300 therethrough.

Then, air flowing into the rotatable duct 130 through the interior flow channel 40 is supplied to the interior of the shoes 300 through the rotatable duct 130. When the first supply portion 90 is not used, the rotatable duct 130 is rotated to the upper side of the receiving portion 50 and, only when the first supply portion 90 is used, the rotatable duct 130 extends to the interior of the receiving portion 50.

In addition, the shoe management apparatus according to the present disclosure is further provided with flow channels for supplying air towards the interior of the shoes 300, whereby the flow rate of air supplied to the interior of the shoes 300 is increased, thereby remarkably reducing time and cost for drying the shoes 300 and for management of the shoes 300, as compared with a structure of simply supplying air from the receiving portion 50 in a direction in which the shoes 300 are placed.

Operation of Second Supply Portion Alone

In the shoe management apparatus according to the present disclosure, the rotatable duct 130 may be disposed as a stationary duct in the first supply portion 90 so as not to be rotated and may be kept in a state of extending towards the interior of the receiving portion 50.

In addition, the second supply portion 180 may be lifted or lowered inside the rotatable duct 130 installed as a stationary duct.

When the shoes 300 are placed in the receiving portion 50, the measurement sensors 232 of the height measurement unit 230 detect the shoes 300 and send a detection result to the controller 240. Since the height measurement unit 230 is provided with the multiple measurement sensors 232 in the vertical direction, the height measurement unit 230 measures the heights of the shoes 300 and sends a measured value to the controller 240.

Based on the measured value of the shoes 300, the controller 240 operates the second driver 186. The controller 240 operates the second driver 186 to move the duct body 182 to the lower side of the rotatable duct 130.

Accordingly, air flowing into the duct body 182 of the second supply portion 180 through the first supply portion 90 is supplied to the interiors of the shoes 300 and dries the shoes 300.

Due to extension of the second supply portion 180 to the lower side of the rotatable duct 130, a flow channel for supplying air to the interiors of the shoes 300 extends. By operation of the second supply portion 180, the flow rate of air supplied to the interior of the shoes 300 is increased, thereby remarkably reducing time and cost for drying the shoes 300 and for management of the shoes 300.

Operation of Second Supply Portion and Third Supply Portion Only

In the shoe management apparatus according to the present disclosure, the rotatable duct 130 may be disposed as a stationary duct in the first supply portion 90 so as not to be rotated and may be kept in a state of extending towards the interior of the receiving portion 50.

In addition, the second supply portion 180 and the third supply portion 200 may be lifted or lowered inside the rotatable duct 130 installed as a stationary duct.

When the shoes 300 are placed in the receiving portion 50, the measurement sensors 232 of the height measurement unit 230 detect the shoes 300 and send a detection result to the controller 240. Since the height measurement unit 230 is provided with the multiple measurement sensors 232 in the vertical direction, the height measurement unit 230 measures the heights of the shoes 300 and sends a measured value to the controller 240.

The controller 240 operates the second driver 186 to allow the duct body 182 to protrude from the lower side of the rotatable duct 130. The screw bar 190 is rotated by rotational force from the second driver 186 to allow the core member 196 engaging with the screw bar 190 through the gears to move downwards along the screw bar 190.

The core member 196 has the threads formed on the hollow inner surface thereof and engaging with the threads formed on the outer surface of the screw bar 190 and the core member 196 is connected to the stationary support 197 such that rotation of the core member 196 can be restricted. The core member 196 is secured to the inner surface of the duct body 182 through the stationary support 197 and the duct body 182 is disposed inside the rotatable duct 130, thereby restricting rotation of the duct body 182.

The duct body 182 is moved downwards through downward movement of the core member 196 and the lower duct 202 disposed at the lower side of the duct body 182 is connected to the lower side of the core member 196 via the rotation-restricting portion 220. Accordingly, the duct body 182 and the lower duct 202 are moved downwards through downward movement of the core member 196.

Accordingly, air flowing to the second supply portion 180 and the third supply portion 200 through the first supply portion 90 is supplied to the interior of the shoes 300 and dries the shoes 300.

Due to extension of the second supply portion 180 and the third supply portion 200 to the lower side of the rotatable duct 130, a flow channel for supplying air to the interior of the shoes 300 extends, whereby the flow rate of air supplied to the interior of the shoes 300 is increased, thereby remarkably reducing time and cost for drying the shoes 300 and for management of the shoes 300.

In addition, when the controller 240 operates the second driver 186 to further move the duct body 182 downwards, the roller member 209 disposed at the lower side of the third supply portion 200 adjoins the insole 302 of the shoe 300 and the third supply portion 200 defines a flow channel in a bent shape.

The third supply portion 200 is slantedly lowered towards the insole 302 of the shoe 300 such that the lower duct 202 is rotated at a predetermined angle about the deformable duct 208 to allow the roller member 209 to adjoin the insole 302. The length of the deformable duct 208 is increased and the rotation-restricting protrusion 222 is moved along the rotation-restricting groove 224 through rotation of the lower duct 202.

The core member 196 has a function of lifting or lowering the second supply portion 180 and the third supply portion 200 and a function of maintaining the shape of the third supply portion 200 disposed in a bent shape.

Accordingly, air flowing to the duct body 182 of the second supply portion 180 through the first supply portion 90 is supplied into the shoes 300 and dries the shoes 300 after sequentially passing through the deformable duct 208 and the lower duct 202.

The third supply portion 200 defines a flow channel in a bent state, thereby enabling uniform and rapid drying of interior of the shoes 300.

Although some embodiments have been described herein with reference to the accompanying drawings, it should be understood that these embodiments are provided for illustration only and are not to be construed in any way as limiting the present disclosure, and that various modifications, changes, alterations, and equivalent embodiments can be made by those skilled in the art without departing from the spirit and scope of the present disclosure.

What is claimed is:

1. A shoe management apparatus, comprising:
  a receiving portion defining a receiving space for receiving shoes therein;
  a first supply portion for guiding flow of a fluid towards the receiving portion, the first supply portion comprising:
    a stationary duct disposed above the receiving space;
    a flexible duct connected to the stationary duct and configured to rotate to change shape;
    a rotatable duct connected to the flexible duct; and
    a first driver connected to the rotatable duct and configured to generate a rotational force to rotate the rotatable duct.

2. The shoe management apparatus according to claim 1, wherein the receiving portion comprises:
  an upper surface disposed in a horizontal direction and formed with a movement hole, the rotatable duct being configured to move within the movement hole; and
  side surfaces disposed under the upper surface at opposing ends of the upper surface, the side surfaces extending in a vertical direction, the vertical direction being perpendicular to the horizontal direction.

3. The shoe management apparatus according to claim 2, wherein the first supply portion further comprises a stationary housing secured to the upper surface of the receiving portion and positioned within the movement hole, the stationary housing including an interior space, and
  wherein the rotatable duct is configured to rotate to be disposed within the interior space of the stationary housing.

4. The shoe management apparatus according to claim 1, wherein the first supply portion further comprises a stationary housing secured to the receiving portion and having an interior space, and
  wherein the rotatable duct is configured to rotate to be disposed within the interior space of the stationary housing.

5. The shoe management apparatus according to claim 4, wherein the stationary housing surrounds at least a portion of the flexible duct, and
  wherein a lower side of the flexible duct is disposed inside the rotatable duct.

6. The shoe management apparatus according to claim 1, wherein the first supply portion further comprises a blower disposed adjacent to the stationary duct and configured to supply the fluid into the stationary duct; and
  wherein the stationary duct comprises:
    a first duct disposed adjacent to the blower and extending in a horizontal direction; and
    a second duct angled downwards from a distal end of the first duct and connected to the flexible duct.

7. The shoe management apparatus according to claim 6, wherein the first duct has a cross-sectional area that gradually increases from the second duct towards the blower.

8. The shoe management apparatus according to claim 1, wherein the flexible duct includes an upper side connected to the stationary duct and a lower side disposed inside the rotatable duct, and
  wherein the flexible duct guides air received through the stationary duct to flow into the rotatable duct.

9. The shoe management apparatus according to claim 1, wherein the flexible duct defines a duct channel having a zigzag shape to allow air to be discharged into the rotatable duct through the flexible duct.

10. The shoe management apparatus according to claim 1, wherein the flexible duct comprises:
  a first flexible tube connected to the stationary duct and including one surface having a concave shape; and
  a second flexible tube connected to the first flexible tube and including one surface having a convex shape, and
  wherein inner channels of the first flexible tube have a same cross-sectional area as inner channels of the second flexible tube.

11. The shoe management apparatus according to claim 1, wherein the first driver includes:
  a motor bracket secured to the receiving portion; and
  a drive motor secured to the motor bracket and axially connected to a rotational center of the rotatable duct to rotate the rotatable duct.

12. A shoe management apparatus, comprising:
  a casing including an electric compartment configured to supply air for drying a shoe;
  a receiving portion positioned within the casing and defining a receiving space for receiving the shoe; and
  a first supply portion guiding a flow of the air towards the receiving portion, the first supply portion comprising:
    a stationary duct disposed above the receiving space;
    a flexible duct connected to the stationary duct and configured to rotate to change shape;
    a rotatable duct connected to the flexible duct; and
    a first driver connected to the rotatable duct and configured to generate a rotational force to rotate the rotatable duct.

13. The shoe management apparatus according to claim 12, wherein the casing further comprises an interior flow channel extending between the electric compartment and the first supply portion such that the air supplied from the electric compartment to the interior flow channel is supplied to the shoe through the first supply portion.

14. The shoe management apparatus according to claim 12, wherein the electric compartment comprises:

a steam generator configured to supply steam to the first supply portion to sterilize the shoe; and a main blower connected to the steam generator and configured to deliver the steam generated by the steam generator to the first supply portion through an interior flow channel disposed inside the casing.

15. The shoe management apparatus according to claim 12, wherein the first supply portion further comprises a stationary housing secured to the receiving portion and having an interior space, and wherein the rotatable duct is configured to rotate to be disposed within the interior space of the stationary housing.

16. The shoe management apparatus according to claim 15, wherein the rotatable duct is operable in a first mode in which the rotatable duct is rotated to be positioned within the interior space of the stationary housing and in a second mode in which the rotatable duct is rotated to be positioned outside the interior space of the stationary housing and into an interior of the receiving space.

17. The shoe management apparatus according to claim 12, wherein the first supply portion further comprises a blower disposed adjacent to the stationary duct and configured to supply the air into the stationary duct.

18. The shoe management apparatus according to claim 17, wherein the first supply portion further comprises a heat exchanger disposed adjacent to the blower and configured to perform heat exchange with the air before flowing into the blower.

19. The shoe management apparatus according to claim 12, wherein the flexible duct defines a duct channel having a zigzag shape to allow the air to be discharged into the rotatable duct through the flexible duct.

20. The shoe management apparatus according to claim 12, wherein the flexible duct comprises:

a first flexible tube connected to the stationary duct and including one surface having a concave shape; and a second flexible tube connected to the first flexible tube and including one surface having a convex shape, and wherein inner channels of the first flexible tube have a same cross-sectional area as inner channels of the second flexible tube.

* * * * *